United States Patent
Park et al.

(10) Patent No.: US 10,266,568 B2
(45) Date of Patent: Apr. 23, 2019

(54) CYCLIC CITRULLINATED PEPTIDE, RHEUMATOID ARTHRITIS DIAGNOSIS COMPOSITION INCLUDING THE SAME, RHEUMATOID ARTHRITIS DIAGNOSIS METHOD USING THE PEPTIDE OR THE COMPOSITION, AND METHOD OF SCREENING DIAGNOSTIC MARKER FOR RHEUMATOID ARTHRITIS

(71) Applicant: KOREA INSTITUTE OF SCIENCE AND TECHNOLOGY, Seoul (KR)

(72) Inventors: Min Park, Seoul (KR); Min-Jung Kang, Seoul (KR); Byung Hwa Jung, Seoul (KR); Young Sook Yoo, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 294 days.

(21) Appl. No.: 14/849,755

(22) Filed: Sep. 10, 2015

(65) Prior Publication Data

US 2016/0280741 A1   Sep. 29, 2016

(30) Foreign Application Priority Data

Mar. 26, 2015 (KR) ........................ 10-2015-0042566

(51) Int. Cl.
  *C07K 7/56* (2006.01)
  *C07K 14/47* (2006.01)
  *G01N 33/68* (2006.01)
  *G01N 33/564* (2006.01)
  *G01N 33/577* (2006.01)

(52) U.S. Cl.
  CPC ............ *C07K 7/56* (2013.01); *C07K 14/4713* (2013.01); *G01N 33/564* (2013.01); *G01N 33/577* (2013.01); *G01N 33/6803* (2013.01); *G01N 2440/18* (2013.01); *G01N 2800/102* (2013.01)

(58) Field of Classification Search
  None
  See application file for complete search history.

(56) References Cited

U.S. PATENT DOCUMENTS

| | | | | |
|---|---|---|---|---|
| 6,596,476 B1 * | 7/2003 | Lesniewski | ........... | C07K 14/005 435/5 |
| 2010/0047819 A1 * | 2/2010 | Scholz | ............. | G01N 33/54313 435/7.1 |
| 2011/0263042 A1 * | 10/2011 | Milne | .................. | G01N 33/564 436/501 |

FOREIGN PATENT DOCUMENTS

| | | | | |
|---|---|---|---|---|
| WO | WO98/22503 | * | 5/1998 | ............. C07K 14/47 |
| WO | 2012/156313 A1 | | 11/2012 | |
| WO | 2013/056377 A1 | | 4/2013 | |

OTHER PUBLICATIONS

Park et al. "Evaluation of a specific diagnostic marker for rheumatoid arthritis based on cyclic citrullinated peptide" Journal of Pharmaceutical and Biomedical Analysis 115 (2015) 107-113, http://dx.doi.org/10.1016/j.jpba.2015.06.032, online Jun. 25, 2015 (Year: 2015).*
Schellekens et al. "Citrulline is an Essential Constituent of Antigenic Determinants Recognized by Rheumatoid Arthritis—specific Autoantibodies" J. Clin. Invest. vol. 101, No. 1, Jan. 1998, 273-281 (Year: 1998).*
Harlow, E. and Lane, D., Antibodies: A Laboratory Manual (1988) Cold Spring Harbor Laboratory Press, Cold Spring Harbor, NY, pp. 23-26 (Year: 1988).*
Lederman et al. "A single amino acid substitution in a common African allele of the CD4 molecule ablates binding of the monoclonal antibody, OKT4" Mol Immunol. Nov. 1991;28(11):1171-81 (Year: 1991).*
Colman et al. Research in Immunology, 1994; 145(1): 33-36 (Year: 1994).*
NCBI Blast, blastp suite-2 sequences, RID-Z4A8MFPT114, retrieved from https://blast.ncbi.nlm.nih.gov/Blast.cgi on Oct. 26, 2017, 8 pages total (Year: 2017).*
Pyun et al. "Performance characteristic of anti-cyclic citrullinated peptide (CCP) assay on Korean rheumatoid arthritis (RA) patients and healthy controls" Journal of Pharmaceutical and Biomedical Analysis 92 (2014) 69-73, Available online Jan. 18, 2014 (Year: 2014).*
Ko et al., Immunostick Assay for Medical Diagnosis of Rheumatoid Althritis, Biotechnology and Bioprocess Engineering, 2011, pp. 1248-1253, vol. 16, Springer.

* cited by examiner

*Primary Examiner* — Christine Foster

(74) *Attorney, Agent, or Firm* — Goldilocks Zone IP Law

(57) ABSTRACT

Rheumatoid arthritis is efficiently diagnosed with improved patient's convenience using a rheumatoid arthritis diagnosis composition and a kit, each including cyclic citrullinated peptide (CCP), a rheumatoid arthritis diagnosis method using the CCP, the rheumatoid arthritis diagnosis composition, or the kit, a method of obtaining information for rheumatoid arthritis diagnosis, and a method of screening a novel diagnostic marker for rheumatoid arthritis.

7 Claims, 21 Drawing Sheets
Specification includes a Sequence Listing.

SEQUENCE LISTING

<160> NUMBER OF SEQ ID NOS: 14

<210> SEQ ID NO 1
<211> LENGTH: 15
<212> TYPE: PRT
<213> ORGANISM: Artificial Sequence
<220> FEATURE:
<223> OTHER INFORMATION: cyclic citrullinated peptide. Xaa indicates
      citrulline, Citrulline is an amino acid resulting from post-
      translational modification of a ketimine group of arginine into a
      ketone group by peptidylarginine deiminase (PAD)

<400> SEQUENCE: 1

His Cys His Gln Glu Ser Thr Xaa Gly Arg Ser Arg Gly Cys Gly
 1               5                  10                  15

<210> SEQ ID NO 2
<211> LENGTH: 7
<212> TYPE: PRT
<213> ORGANISM: Homo sapiens

<400> SEQUENCE: 2

Glu Gly Leu His Asn His Tyr
 1               5

<210> SEQ ID NO 3
<211> LENGTH: 15
<212> TYPE: PRT
<213> ORGANISM: Artificial Sequence
<220> FEATURE:
<223> OTHER INFORMATION: cyclic citrullinated peptide. Xaa indicates
      citrulline, Citrulline is an amino acid resulting from post-
      translational modification of a ketimine group of arginine into a
      ketone group by peptidylarginine deiminase (PAD)

<400> SEQUENCE: 3

His Ser His Gln Glu Ser Thr Xaa Gly Arg Ser Arg Gly Ser Gly
 1               5                  10                  15

<210> SEQ ID NO 4
<211> LENGTH: 17
<212> TYPE: PRT
<213> ORGANISM: Artificial Sequence

```
<220> FEATURE:
<223> OTHER INFORMATION: cyclic citrullinated peptide. Xaa indicates
      citrulline, Citrulline is an amino acid resulting from post-
      translational modification of a ketimine group of arginine into a
      ketone group by peptidylarginine deiminase (PAD)

<400> SEQUENCE: 4

Glx Glx His Ser His Gln Glu Ser Thr Xaa Gly Arg Ser Arg Gly Ser
 1               5                  10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: cyclic citrullinated peptide. Xaa indicates
      citrulline, Citrulline is an amino acid resulting from post-
      translational modification of a ketimine group of arginine into a
      ketone group by peptidylarginine deiminase (PAD)

<400> SEQUENCE: 5

His Ser His Gln Glu Ser Thr Xaa Gly Arg Ser Arg Gly Ser Gly Glx
 1               5                  10                  15

Glx

<210> SEQ ID NO 6
<211> LENGTH: 19
<212> TYPE: PRT
<213> ORGANISM: Artificial Sequence
<220> FEATURE:
<223> OTHER INFORMATION: cyclic citrullinated peptide. Xaa indicates
      citrulline, Citrulline is an amino acid resulting from post-
      translational modification of a ketimine group of arginine into a
      ketone group by peptidylarginine deiminase (PAD)

<400> SEQUENCE: 6

Glx Glx His Ser His Gln Glu Ser Thr Xaa Gly Arg Ser Arg Gly Ser
 1               5                  10                  15

Gly Glx Glx

<210> SEQ ID NO 7
<211> LENGTH: 15
<212> TYPE: PRT
<213> ORGANISM: Artificial Sequence
<220> FEATURE:
<223> OTHER INFORMATION: cyclic citrullinated peptide. Xaa indicates
      citrulline, Citrulline is an amino acid resulting from post-
      translational modification of a ketimine group of arginine into a
      ketone group by peptidylarginine deiminase (PAD)

<400> SEQUENCE: 7

His Cys His Gln Glu Ser Thr Xaa Gly Pro Ser Arg Gly Cys Gly
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: cyclic citrullinated peptide. Xaa indicates
      citrulline, Citrulline is an amino acid resulting from post-
      translational modification of a ketimine group of arginine into a
      ketone group by peptidylarginine deiminase (PAD)
```

```
<400> SEQUENCE: 8

His Cys His Gln Glu Ser Thr Xaa Gly Arg Ala Arg Gly Cys Gly
 1               5                  10                  15

<210> SEQ ID NO 9
<211> LENGTH: 15
<212> TYPE: PRT
<213> ORGANISM: Artificial Sequence
<220> FEATURE:
<223> OTHER INFORMATION: cyclic citrullinated peptide. Xaa indicates
      citrulline, Citrulline is an amino acid resulting from post-
      translational modification of a ketimine group of arginine into a
      ketone group by peptidylarginine deiminase (PAD)

<400> SEQUENCE: 9

His Cys His Gln Glu Ser Thr Xaa Gly Arg Ser Pro Gly Cys Gly
 1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: cyclic citrullinated peptide. Xaa indicates
      citrulline, Citrulline is an amino acid resulting from post-
      translational modification of a ketimine group of arginine into a
      ketone group by peptidylarginine deiminase (PAD)

<400> SEQUENCE: 10

His Cys His Gln Glu Ser Thr Xaa Gly Pro Ala Pro Gly Cys Gly
 1               5                  10                  15

<210> SEQ ID NO 11
<211> LENGTH: 663
<212> TYPE: PRT
<213> ORGANISM: Homo sapiens

<400> SEQUENCE: 11

Met Ala Pro Lys Arg Val Val Gln Leu Ser Leu Lys Met Pro Thr His
 1               5                  10                  15

Ala Val Cys Val Val Gly Val Glu Ala His Val Asp Ile His Ser Asp
                20                  25                  30

Val Pro Lys Gly Ala Asn Ser Phe Arg Val Ser Gly Ser Ser Gly Val
            35                  40                  45

Glu Val Phe Met Val Tyr Asn Arg Thr Arg Val Lys Glu Pro Ile Gly
         50                  55                  60

Lys Ala Arg Trp Pro Leu Asp Thr Asp Ala Asp Met Val Val Ser Val
 65                  70                  75                  80

Gly Thr Ala Ser Lys Glu Leu Lys Asp Phe Lys Val Arg Val Ser Tyr
                85                  90                  95

Phe Gly Glu Gln Glu Asp Gln Ala Leu Gly Arg Ser Val Leu Tyr Leu
            100                 105                 110

Thr Gly Val Asp Ile Ser Leu Glu Val Asp Thr Gly Arg Thr Gly Lys
        115                 120                 125

Val Lys Arg Ser Gln Gly Asp Lys Lys Thr Trp Arg Trp Gly Pro Glu
    130                 135                 140

Gly Tyr Gly Ala Ile Leu Leu Val Asn Cys Asp Arg Asp Asn His Arg
145                 150                 155                 160

Ser Ala Glu Pro Asp Leu Thr His Ser Trp Leu Met Ser Leu Ala Asp
                165                 170                 175
```

-continued

```
Leu Gln Asp Met Ser Pro Met Leu Leu Ser Cys Asn Gly Pro Asp Lys
            180                 185                 190

Leu Phe Asp Ser His Lys Leu Val Leu Asn Val Pro Phe Ser Asp Ser
        195                 200                 205

Lys Arg Val Arg Val Phe Cys Ala Arg Gly Gly Asn Ser Leu Ser Asp
    210                 215                 220

Tyr Lys Gln Val Leu Gly Pro Gln Cys Leu Ser Tyr Glu Val Glu Arg
225                 230                 235                 240

Gln Pro Gly Glu Gln Glu Ile Lys Phe Tyr Val Glu Gly Leu Thr Phe
                245                 250                 255

Pro Asp Ala Asp Phe Leu Gly Leu Val Ser Leu Ser Val Ser Leu Val
            260                 265                 270

Asp Pro Gly Thr Leu Pro Glu Val Thr Leu Phe Thr Asp Thr Val Gly
        275                 280                 285

Phe Arg Met Ala Pro Trp Ile Met Thr Pro Asn Thr Gln Pro Pro Glu
    290                 295                 300

Glu Leu Tyr Val Cys Arg Val Met Asp Thr His Gly Ser Asn Glu Lys
305                 310                 315                 320

Phe Leu Glu Asp Met Ser Tyr Leu Thr Leu Lys Ala Asn Cys Lys Leu
                325                 330                 335

Thr Ile Cys Pro Gln Val Glu Asn Arg Asn Asp Arg Trp Ile Gln Asp
            340                 345                 350

Glu Met Glu Phe Gly Tyr Ile Glu Ala Pro His Lys Ser Phe Pro Val
        355                 360                 365

Val Phe Asp Ser Pro Arg Asn Arg Gly Leu Lys Asp Phe Pro Tyr Lys
    370                 375                 380

Arg Ile Leu Gly Pro Asp Phe Gly Tyr Val Thr Arg Glu Ile Pro Leu
385                 390                 395                 400

Pro Gly Pro Ser Ser Leu Asp Ser Phe Gly Asn Leu Asp Val Ser Pro
                405                 410                 415

Pro Val Thr Val Gly Gly Thr Glu Tyr Pro Leu Gly Arg Ile Leu Ile
            420                 425                 430

Gly Ser Ser Phe Pro Lys Ser Gly Gly Arg Gln Met Ala Arg Ala Val
        435                 440                 445

Arg Asn Phe Leu Lys Ala Gln Gln Val Gln Ala Pro Val Glu Leu Tyr
    450                 455                 460

Ser Asp Trp Leu Ser Val Gly His Val Asp Glu Phe Leu Thr Phe Val
465                 470                 475                 480

Pro Thr Ser Asp Gln Lys Gly Phe Arg Leu Leu Leu Ala Ser Pro Ser
                485                 490                 495

Ala Cys Leu Lys Leu Phe Gln Glu Lys Lys Glu Gly Tyr Gly Glu
            500                 505                 510

Ala Ala Gln Phe Asp Gly Leu Lys His Gln Ala Lys Arg Ser Ile Asn
        515                 520                 525

Glu Met Leu Ala Asp Arg His Leu Gln Arg Asp Asn Leu His Ala Gln
    530                 535                 540

Lys Cys Ile Asp Trp Asn Arg Asn Val Leu Lys Arg Glu Leu Gly Leu
545                 550                 555                 560

Ala Glu Ser Asp Ile Val Asp Ile Pro Gln Leu Phe Phe Leu Lys Asn
                565                 570                 575

Phe Tyr Ala Glu Ala Phe Phe Pro Asp Met Val Asn Met Val Val Leu
            580                 585                 590
```

```
Gly Lys Tyr Leu Gly Ile Pro Lys Pro Tyr Gly Pro Ile Ile Asn Gly
            595                 600                 605

Arg Cys Cys Leu Glu Glu Lys Val Gln Ser Leu Leu Glu Pro Leu Gly
610                 615                 620

Leu His Cys Ile Phe Ile Asp Asp Tyr Leu Ser Tyr His Glu Leu Gln
625                 630                 635                 640

Gly Glu Ile His Cys Gly Thr Asn Val Arg Arg Lys Pro Phe Pro Phe
                645                 650                 655

Lys Trp Trp Asn Met Val Pro
            660

<210> SEQ ID NO 12
<211> LENGTH: 665
<212> TYPE: PRT
<213> ORGANISM: Homo sapiens

<400> SEQUENCE: 12

Met Leu Arg Glu Arg Thr Val Arg Leu Gln Tyr Gly Ser Arg Val Glu
  1               5                  10                  15

Ala Val Tyr Val Leu Gly Thr Tyr Leu Trp Thr Asp Val Tyr Ser Ala
                 20                  25                  30

Ala Pro Ala Gly Ala Gln Thr Phe Ser Leu Lys His Ser Glu His Val
             35                  40                  45

Trp Val Glu Val Arg Asp Gly Glu Ala Glu Val Ala Thr Asn
         50                  55                  60

Gly Lys Gln Arg Trp Leu Leu Ser Pro Ser Thr Thr Leu Arg Val Thr
 65                  70                  75                  80

Met Ser Gln Ala Ser Thr Glu Ala Ser Ser Asp Lys Val Thr Val Asn
                 85                  90                  95

Tyr Tyr Asp Glu Glu Gly Ser Ile Pro Ile Asp Gln Ala Gly Leu Phe
                100                 105                 110

Leu Thr Ala Ile Glu Ile Ser Leu Asp Val Asp Ala Asp Arg Asp Gly
            115                 120                 125

Val Val Glu Lys Asn Asn Pro Lys Lys Ala Ser Trp Thr Trp Gly Pro
        130                 135                 140

Glu Gly Gln Gly Ala Ile Leu Leu Val Asn Cys Asp Arg Glu Thr Pro
145                 150                 155                 160

Trp Leu Pro Lys Glu Asp Cys Arg Asp Gly Lys Val Tyr Ser Lys Glu
                165                 170                 175

Asp Leu Lys Asp Met Ser Gln Met Ile Leu Arg Thr Lys Gly Pro Asp
            180                 185                 190

Arg Leu Pro Ala Gly Tyr Glu Ile Val Leu Tyr Ile Ser Met Ser Asp
        195                 200                 205

Ser Asp Lys Val Gly Val Phe Tyr Val Glu Asn Pro Phe Phe Gly Gln
    210                 215                 220

Arg Tyr Ile His Ile Leu Gly Arg Arg Lys Leu Tyr His Val Val Lys
225                 230                 235                 240

Tyr Thr Gly Gly Ser Ala Glu Leu Leu Phe Val Gly Leu Cys
                245                 250                 255

Phe Pro Asp Glu Gly Phe Ser Gly Leu Val Ser Ile His Val Ser Leu
            260                 265                 270

Leu Glu Tyr Met Ala Gln Asp Ile Pro Leu Thr Pro Ile Phe Thr Asp
        275                 280                 285
```

```
Thr Val Ile Phe Arg Ile Ala Pro Trp Ile Met Thr Pro Asn Ile Leu
    290                 295                 300
Pro Pro Val Ser Val Phe Val Cys Cys Met Lys Asp Asn Tyr Leu Phe
305                 310                 315                 320
Leu Lys Glu Val Lys Asn Leu Val Glu Lys Thr Asn Cys Glu Leu Lys
                325                 330                 335
Val Cys Phe Gln Tyr Leu Asn Arg Gly Asp Arg Trp Ile Gln Asp Glu
                340                 345                 350
Ile Glu Phe Gly Tyr Ile Glu Ala Pro His Lys Gly Phe Pro Val Val
            355                 360                 365
Leu Asp Ser Pro Arg Asp Gly Asn Leu Lys Asp Phe Pro Val Lys Glu
370                 375                 380
Leu Leu Gly Pro Asp Phe Gly Tyr Val Thr Arg Glu Pro Leu Phe Glu
385                 390                 395                 400
Ser Val Thr Ser Leu Asp Ser Phe Gly Asn Leu Glu Val Ser Pro Pro
                405                 410                 415
Val Thr Val Asn Gly Lys Thr Tyr Pro Leu Gly Arg Ile Leu Ile Gly
                420                 425                 430
Ser Ser Phe Pro Leu Ser Gly Gly Arg Arg Met Thr Lys Val Val Arg
            435                 440                 445
Asp Phe Leu Lys Ala Gln Gln Val Gln Ala Pro Val Glu Leu Tyr Ser
450                 455                 460
Asp Trp Leu Thr Val Gly His Val Asp Glu Phe Met Ser Phe Val Pro
465                 470                 475                 480
Ile Pro Gly Thr Lys Lys Phe Leu Leu Leu Met Ala Ser Thr Ser Ala
                485                 490                 495
Cys Tyr Lys Leu Phe Arg Glu Lys Gln Lys Asp Gly His Gly Glu Ala
            500                 505                 510
Ile Met Phe Lys Gly Leu Gly Gly Met Ser Ser Lys Arg Ile Thr Ile
            515                 520                 525
Asn Lys Ile Leu Ser Asn Glu Ser Leu Val Gln Glu Asn Leu Tyr Phe
530                 535                 540
Gln Arg Cys Leu Asp Trp Asn Arg Asp Ile Leu Lys Lys Glu Leu Gly
545                 550                 555                 560
Leu Thr Glu Gln Asp Ile Ile Asp Leu Pro Ala Leu Phe Lys Met Asp
                565                 570                 575
Glu Asp His Arg Ala Arg Ala Phe Phe Pro Asn Met Val Asn Met Ile
            580                 585                 590
Val Leu Asp Lys Asp Leu Gly Ile Pro Lys Pro Phe Gly Pro Gln Val
            595                 600                 605
Glu Glu Glu Cys Cys Leu Glu Met His Val Arg Gly Leu Leu Glu Pro
610                 615                 620
Leu Gly Leu Glu Cys Thr Phe Ile Asp Asp Ile Ser Ala Tyr His Lys
625                 630                 635                 640
Phe Leu Gly Glu Val His Cys Gly Thr Asn Val Arg Arg Lys Pro Phe
                645                 650                 655
Thr Phe Lys Trp Trp His Met Val Pro
                660                 665

<210> SEQ ID NO 13
<211> LENGTH: 664
<212> TYPE: PRT
<213> ORGANISM: Homo sapiens
```

<400> SEQUENCE: 13

```
Met Ser Leu Gln Arg Ile Val Arg Val Ser Leu Glu His Pro Thr Ser
 1               5                  10                  15

Ala Val Cys Val Ala Gly Val Glu Thr Leu Val Asp Ile Tyr Gly Ser
            20                  25                  30

Val Pro Glu Gly Thr Glu Met Phe Glu Val Tyr Gly Thr Pro Gly Val
        35                  40                  45

Asp Ile Tyr Ile Ser Pro Asn Met Glu Arg Gly Arg Glu Arg Ala Asp
    50                  55                  60

Thr Arg Arg Trp Arg Phe Asp Ala Thr Leu Glu Ile Ile Val Val Met
65                  70                  75                  80

Asn Ser Pro Ser Asn Asp Leu Asn Asp Ser His Val Gln Ile Ser Tyr
                85                  90                  95

His Ser Ser His Glu Pro Leu Pro Leu Ala Tyr Ala Val Leu Tyr Leu
            100                 105                 110

Thr Cys Val Asp Ile Ser Leu Asp Cys Asp Leu Asn Cys Glu Gly Arg
        115                 120                 125

Gln Asp Arg Asn Phe Val Asp Lys Arg Gln Trp Val Trp Gly Pro Ser
    130                 135                 140

Gly Tyr Gly Gly Ile Leu Leu Val Asn Cys Asp Arg Asp Pro Ser
145                 150                 155                 160

Cys Asp Val Gln Asp Asn Cys Asp Gln His Val His Cys Leu Gln Asp
                165                 170                 175

Leu Glu Asp Met Ser Val Met Val Leu Arg Thr Gln Gly Pro Ala Ala
            180                 185                 190

Leu Phe Asp Asp His Lys Leu Val Leu His Thr Ser Ser Tyr Asp Ala
        195                 200                 205

Lys Arg Ala Gln Val Phe His Ile Cys Gly Pro Glu Asp Val Cys Glu
    210                 215                 220

Ala Tyr Arg His Val Leu Gly Gln Asp Lys Val Ser Tyr Glu Val Pro
225                 230                 235                 240

Arg Leu His Gly Asp Glu Glu Arg Phe Phe Val Glu Gly Leu Ser Phe
                245                 250                 255

Pro Asp Ala Gly Phe Thr Gly Leu Ile Ser Phe His Val Thr Leu Leu
            260                 265                 270

Asp Asp Ser Asn Glu Asp Phe Ser Ala Ser Pro Ile Phe Thr Asp Thr
        275                 280                 285

Val Val Phe Arg Val Ala Pro Trp Ile Met Thr Pro Ser Thr Leu Pro
    290                 295                 300

Pro Leu Glu Val Tyr Val Cys Arg Val Arg Asn Asn Thr Cys Phe Val
305                 310                 315                 320

Asp Ala Val Ala Glu Leu Ala Arg Lys Ala Gly Cys Lys Leu Thr Ile
                325                 330                 335

Cys Pro Gln Ala Glu Asn Arg Asn Asp Arg Trp Ile Gln Asp Glu Met
            340                 345                 350

Glu Leu Gly Tyr Val Gln Ala Pro His Lys Thr Leu Pro Val Val Phe
        355                 360                 365

Asp Ser Pro Arg Asn Gly Glu Leu Gln Asp Phe Pro Tyr Lys Arg Ile
    370                 375                 380

Leu Gly Pro Asp Phe Gly Tyr Val Thr Arg Glu Pro Arg Asp Arg Ser
385                 390                 395                 400

Val Ser Gly Leu Asp Ser Phe Gly Asn Leu Glu Val Ser Pro Pro Val
                405                 410                 415
```

```
Val Ala Asn Gly Lys Glu Tyr Pro Leu Gly Arg Ile Leu Ile Gly Gly
                420                 425                 430

Asn Leu Pro Gly Ser Ser Gly Arg Arg Val Thr Gln Val Val Arg Asp
            435                 440                 445

Phe Leu His Ala Gln Lys Val Gln Pro Val Glu Leu Phe Val Asp
        450                 455                 460

Trp Leu Ala Val Gly His Val Asp Glu Phe Leu Ser Phe Val Pro Ala
465                 470                 475                 480

Pro Asp Gly Lys Gly Phe Arg Met Leu Leu Ala Ser Pro Gly Ala Cys
                485                 490                 495

Phe Lys Leu Phe Gln Glu Lys Gln Lys Cys Gly His Gly Arg Ala Leu
            500                 505                 510

Leu Phe Gln Gly Val Val Asp Asp Glu Gln Val Lys Thr Ile Ser Ile
        515                 520                 525

Asn Gln Val Leu Ser Asn Lys Asp Leu Ile Asn Tyr Asn Lys Phe Val
530                 535                 540

Gln Ser Cys Ile Asp Trp Asn Arg Glu Val Leu Lys Arg Glu Leu Gly
545                 550                 555                 560

Leu Ala Glu Cys Asp Ile Ile Asp Ile Pro Gln Leu Phe Lys Thr Glu
                565                 570                 575

Arg Lys Lys Ala Thr Ala Phe Phe Pro Asp Leu Val Asn Met Leu Val
            580                 585                 590

Leu Gly Lys His Leu Gly Ile Pro Lys Pro Phe Gly Pro Ile Ile Asn
        595                 600                 605

Gly Cys Cys Cys Leu Glu Glu Lys Val Arg Ser Leu Leu Glu Pro Leu
610                 615                 620

Gly Leu His Cys Thr Phe Ile Asp Asp Phe Thr Pro Tyr His Met Leu
625                 630                 635                 640

His Gly Glu Val His Cys Gly Thr Asn Val Cys Arg Lys Pro Phe Ser
                645                 650                 655

Phe Lys Trp Trp Asn Met Val Pro
            660

<210> SEQ ID NO 14
<211> LENGTH: 663
<212> TYPE: PRT
<213> ORGANISM: Homo sapiens

<400> SEQUENCE: 14

Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
                20                  25                  30

Ala Pro Glu Asp Cys Thr Ser Phe Ser Ile Asn Ala Ser Pro Gly Val
            35                  40                  45

Val Val Asp Ile Ala His Gly Pro Pro Ala Lys Lys Lys Ser Thr Gly
        50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Glu Ile Ser Leu Cys Ala Asp Ile Thr Arg Thr Gly Lys Val Lys
        115                 120                 125
```

-continued

```
Pro Thr Arg Ala Val Lys Asp Gln Arg Thr Trp Thr Trp Gly Pro Cys
    130                 135                 140
Gly Gln Gly Ala Ile Leu Leu Val Asn Cys Asp Arg Asp Asn Leu Glu
145                 150                 155                 160
Ser Ser Ala Met Asp Cys Glu Asp Asp Glu Val Leu Asp Ser Glu Asp
                165                 170                 175
Leu Gln Asp Met Ser Leu Met Thr Leu Ser Thr Lys Thr Pro Lys Asp
                180                 185                 190
Phe Phe Thr Asn His Thr Leu Val Leu His Val Ala Arg Ser Glu Met
            195                 200                 205
Asp Lys Val Arg Val Phe Gln Ala Thr Arg Gly Lys Leu Ser Ser Lys
210                 215                 220
Cys Ser Val Val Leu Gly Pro Lys Trp Pro Ser His Tyr Leu Met Val
225                 230                 235                 240
Pro Gly Gly Lys His Asn Met Asp Phe Tyr Val Glu Ala Leu Ala Phe
                245                 250                 255
Pro Asp Thr Asp Phe Pro Gly Leu Ile Thr Leu Thr Ile Ser Leu Leu
                260                 265                 270
Asp Thr Ser Asn Leu Glu Leu Pro Glu Ala Val Val Phe Gln Asp Ser
        275                 280                 285
Val Val Phe Arg Val Ala Pro Trp Ile Met Thr Pro Asn Thr Gln Pro
290                 295                 300
Pro Gln Glu Val Tyr Ala Cys Ser Ile Phe Glu Asn Glu Asp Phe Leu
305                 310                 315                 320
Lys Ser Val Thr Thr Leu Ala Met Lys Ala Lys Cys Lys Leu Thr Ile
                325                 330                 335
Cys Pro Glu Glu Asn Met Asp Asp Gln Trp Met Gln Asp Glu Met
                340                 345                 350
Glu Ile Gly Tyr Ile Gln Ala Pro His Lys Thr Leu Pro Val Val Phe
        355                 360                 365
Asp Ser Pro Arg Asn Arg Gly Leu Lys Glu Phe Pro Ile Lys Arg Val
    370                 375                 380
Met Gly Pro Asp Phe Gly Tyr Val Thr Arg Gly Pro Gln Thr Gly Gly
385                 390                 395                 400
Ile Ser Gly Leu Asp Ser Phe Gly Asn Leu Glu Val Ser Pro Pro Val
                405                 410                 415
Thr Val Arg Gly Lys Glu Tyr Pro Leu Gly Arg Ile Leu Phe Gly Asp
                420                 425                 430
Ser Cys Tyr Pro Ser Asn Asp Ser Arg Gln Met His Gln Ala Leu Gln
            435                 440                 445
Asp Phe Leu Ser Ala Gln Gln Val Gln Ala Pro Val Lys Leu Tyr Ser
    450                 455                 460
Asp Trp Leu Ser Val Gly His Val Asp Glu Phe Leu Ser Phe Val Pro
465                 470                 475                 480
Ala Pro Asp Arg Lys Gly Phe Arg Leu Leu Leu Ala Ser Pro Arg Ser
                485                 490                 495
Cys Tyr Lys Leu Phe Gln Glu Gln Gln Asn Glu Gly His Gly Glu Ala
                500                 505                 510
Leu Leu Phe Glu Gly Ile Lys Lys Lys Gln Gln Lys Ile Lys Asn
            515                 520                 525
Ile Leu Ser Asn Lys Thr Leu Arg Glu His Asn Ser Phe Val Glu Arg
    530                 535                 540
```

-continued

```
Cys Ile Asp Trp Asn Arg Glu Leu Leu Lys Arg Glu Leu Gly Leu Ala
545                 550                 555                 560

Glu Ser Asp Ile Ile Asp Ile Pro Gln Leu Phe Lys Leu Lys Glu Phe
                565             570                 575

Ser Lys Ala Glu Ala Phe Phe Pro Asn Met Val Asn Met Leu Val Leu
            580             585                 590

Gly Lys His Leu Gly Ile Pro Lys Pro Phe Gly Pro Val Ile Asn Gly
        595             600             605

Arg Cys Cys Leu Glu Glu Lys Val Cys Ser Leu Leu Glu Pro Leu Gly
    610             615             620

Leu Gln Cys Thr Phe Ile Asn Asp Phe Phe Thr Tyr His Ile Arg His
625             630             635             640

Gly Glu Val His Cys Gly Thr Asn Val Arg Arg Lys Pro Phe Ser Phe
            645             650             655

Lys Trp Trp Asn Met Val Pro
            660
```

CYCLIC CITRULLINATED PEPTIDE, RHEUMATOID ARTHRITIS DIAGNOSIS COMPOSITION INCLUDING THE SAME, RHEUMATOID ARTHRITIS DIAGNOSIS METHOD USING THE PEPTIDE OR THE COMPOSITION, AND METHOD OF SCREENING DIAGNOSTIC MARKER FOR RHEUMATOID ARTHRITIS

RELATED APPLICATIONS

This application claims the benefit of Korean Patent Application No. 10-2015-0042566, filed on Mar. 26, 2015, in the Korean Intellectual Property Office, the disclosure of which is incorporated herein in its entirety by reference.

BACKGROUND

1. Field

One or more embodiments of the present invention relate to a cyclic citrullinated peptide (CCP), a rheumatoid arthritis diagnosis composition and kit each including the CCP, a rheumatoid arthritis diagnosis method using the CCP, the rheumatoid arthritis diagnosis composition or kit, and a method of screening a diagnostic marker for rheumatoid arthritis.

2. Description of the Related Art

Rheumatoid arthritis ("RA") is a chronic, inflammatory disease that may occur due to autoimmunization of unknown cause. The onset of RA may cause inflammation and pain in the intraarticular synovium (synovial membrane). Sustained pain from RA may make the inflammatory synovial tissue grow into bone and cartilage, and thus may lead to articular deformation and finally behavior disorder. Although no drug for complete cure of RA is available yet, neglecting such symptoms of RA for a long time since its onset may cause articular deformation and spread of inflammation that may damage other organs. Accordingly, it is very crucial to early diagnose and treat RA.

Since an accurate diagnostic method for RA is not currently available, diagnosis for RA is based on a comprehensive analysis of pathognomonic symptoms, test results, and the like. However, systemic lupus erythemathode (SLE), arthralgia, or osteoarthritis (OA) patients with similar symptoms to RA may be confused with early-stage RA patients, and accurate diagnosis for RA is still difficult.

Currently available diagnostic markers for RA include a rheumatoid factor (RF) and an anti-CCP antibody. However, these diagnostic markers have a lower specificity with respect to non-rheumatoid arthritis patients than to normal patients. Therefore, there are needs to discover novel RA diagnostic markers with a high sensitivity and a high specificity with respect to non-rheumatoid arthritis and to develop a diagnostic method for RA by using such novel diagnostic markers.

SUMMARY

One or more embodiments of the present invention include a cyclic citrullinated peptide (CCP).

One or more embodiments of the present invention include a rheumatoid arthritis (RA) diagnosis composition including the CCP.

One or more embodiments of the present invention include an anti-CCP antibody detection method for diagnosis of rheumatoid arthritis (RA) in a subject.

One or more embodiments of the present invention include a method of screening a diagnostic marker for RA.

Additional aspects will be set forth in part in the description which follows and, in part, will be apparent from the description, or may be learned by practice of the presented embodiments.

According to one or more embodiments of the present invention, there is provided a peptide having an amino acid sequence with a sequence identity of about 80% or more to at least one of amino acid sequences of SEQ ID NOS: 3 to 10.

According to one or more embodiments of the present invention, a rheumatoid arthritis diagnosis composition includes a peptide having an amino acid sequence with a sequence identity of about 80% or more to at least one of amino acid sequences of SEQ ID NOs: 3 to 10.

According to one or more embodiments of the present invention, a method of detecting an anti-CCP antibody includes: forming an anti-CCP antibody-peptide complex by contacting a sample taken from a subject and a peptide having an amino acid sequence with a sequence identity of about 80% or more to at least one of amino acid sequences of SEQ ID NOs: 3 to 10 to bind an anti-cyclic citrullinated peptide (CCP) antibody present in the sample to the peptide; and detecting a level of the anti-CCP antibody-peptide complex in the sample.

According to one or more embodiments of the present invention, a method of screening a diagnostic marker for rheumatoid arthritis includes: modifying at least one amino acid of a cyclic citrullinated peptide (CCP) present between citrulline and disulfide bond-forming cycteine in a C-terminal direction from the citrulline; forming anti-CCP antibody-peptide complexes by bringing the modified CCP to contact a test sample taken from a rheumatoid arthritis patient and a control group sample to bind the modified CCP to anti-CCP antibodies present in the test sample and the control sample group; measuring levels of the anti-CCP antibodies in the anti-CCP antibody-peptide complexes in the test sample and the control group sample; and determining the CCP as a candidate diagnostic marker for rheumatoid arthritis if the level of the anti-CCP antibody in the anti-CCP antibody-peptide complex in the test sample is higher than that in the control group sample.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
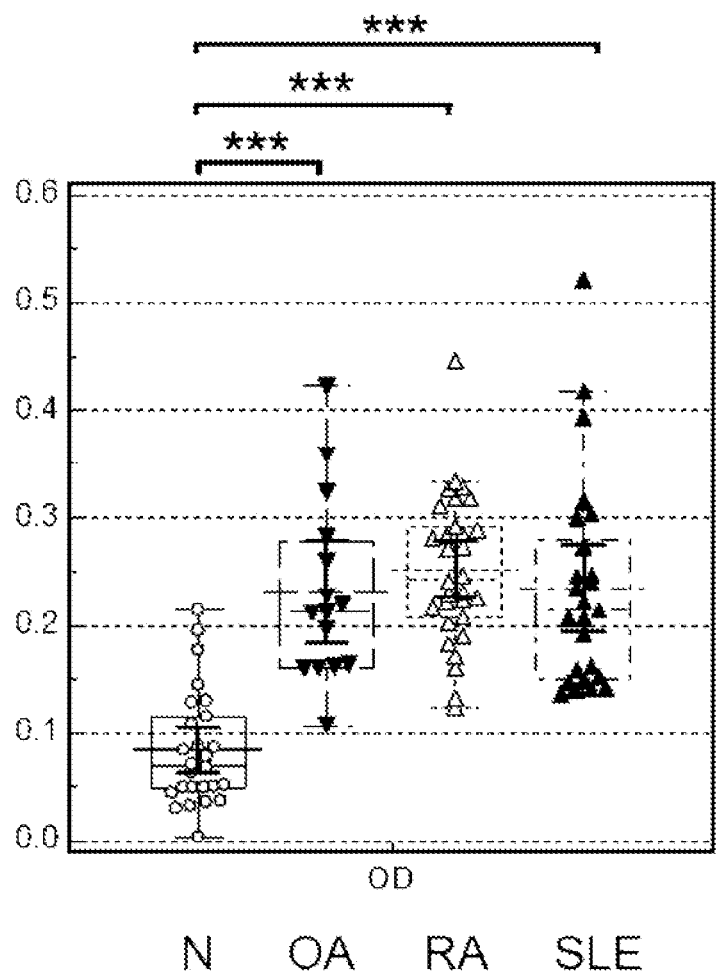
FIGS. 1A to 1F are graphs illustrating the autoimmune antibody levels in blood of the normal patients, osteoarthritis patients, systemic lupus erythemathode (SLE) patients, and rheumatoid arthritis (RA) patients, as results of assay using cyclic citrullinated peptide (CCP, FIG. 1A), a rheumatoid factor (RF, FIG. 1B), and modified CCPs without (FIG. 1C) or with aminocaproic acid (FIGS. 1D to 1F)
Figure 1B:
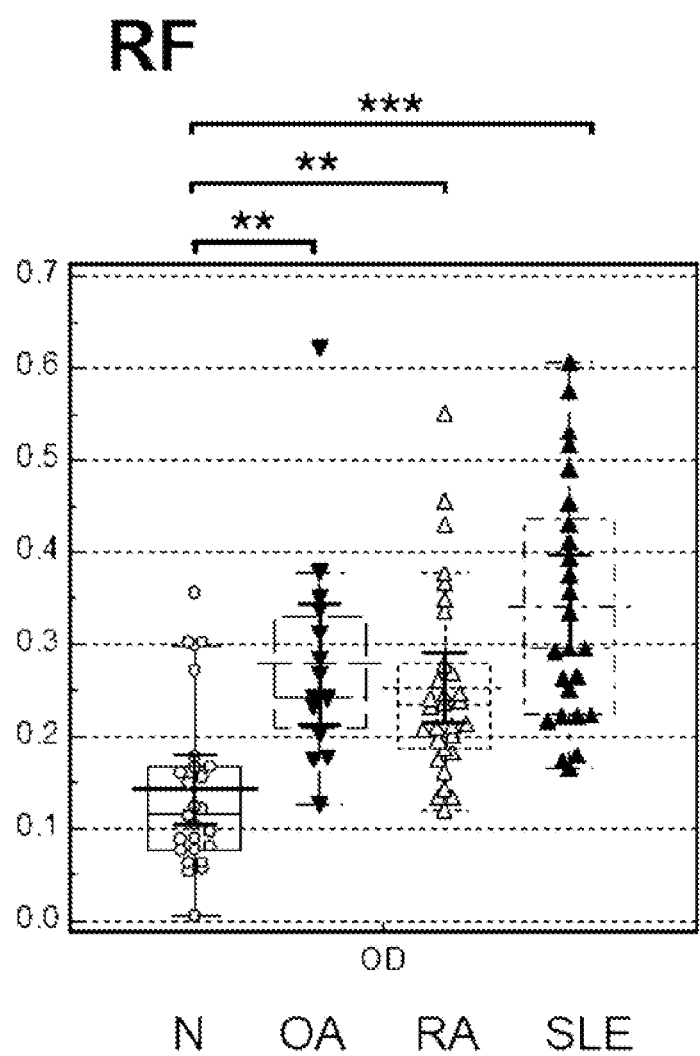
Figure 1C:
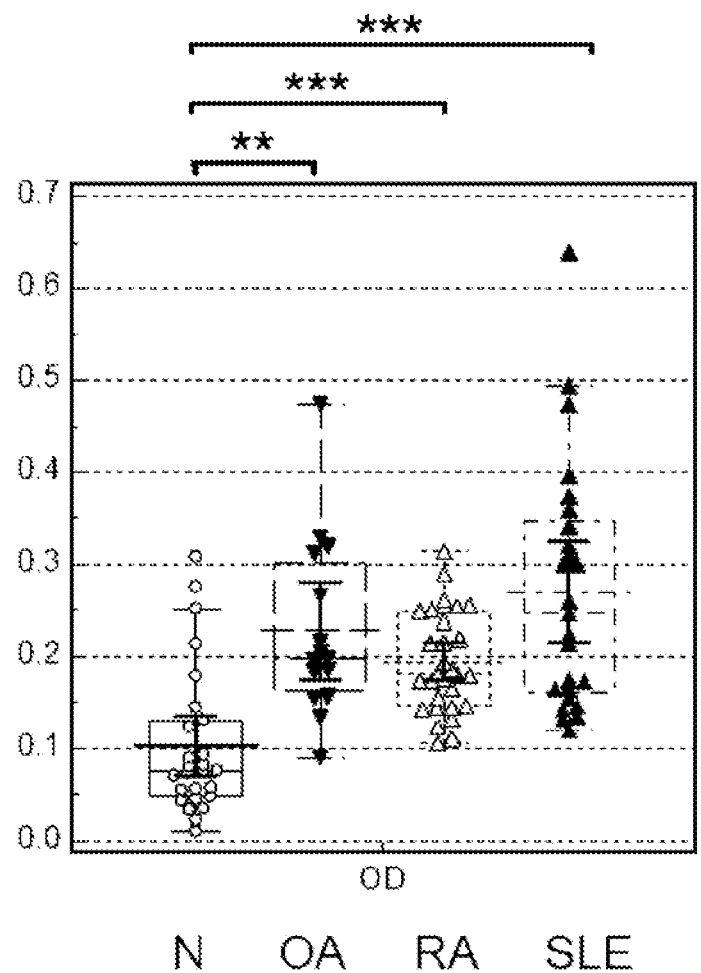
Figure 1D:
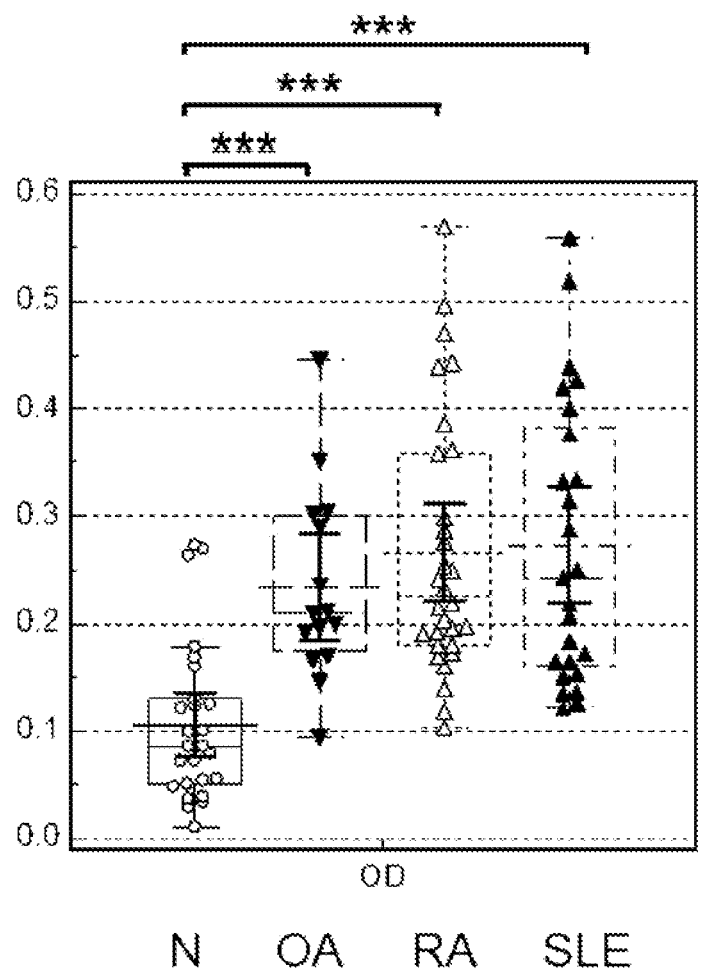
Figure 1E:
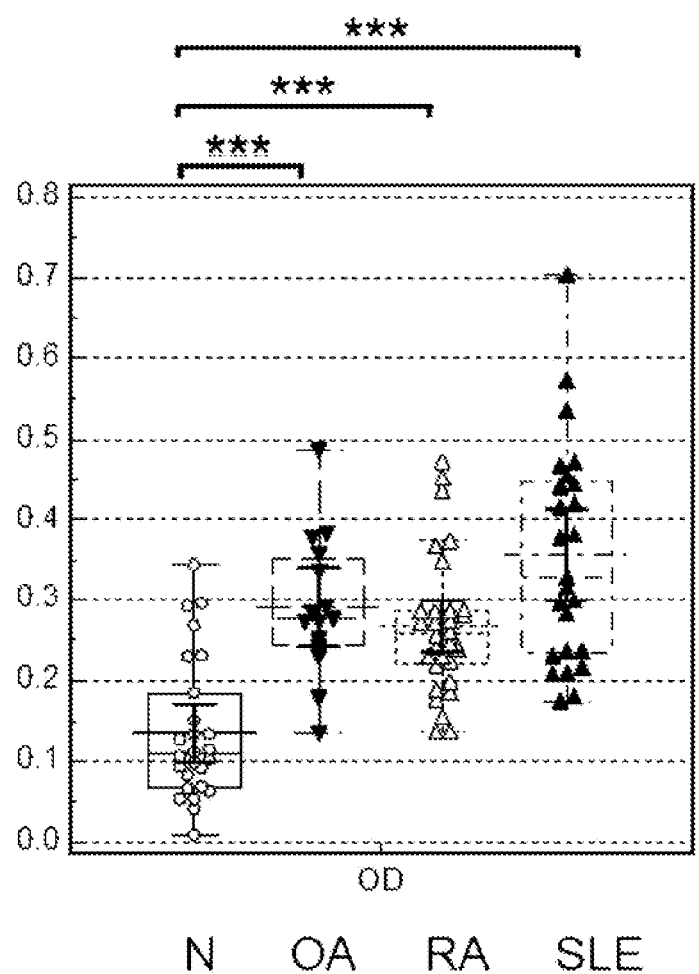
Figure 1F:
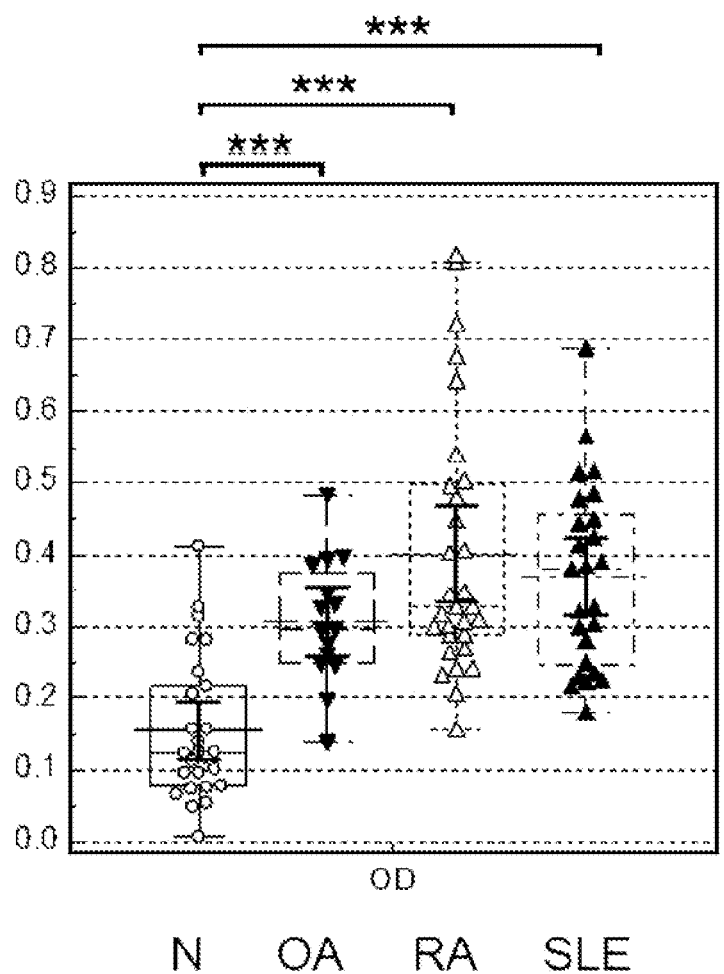

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

As used herein, the term "amino acid" may include the 22 standard amino acids naturally incorporated into peptides, and D-isomers and modified amino acids thereof.

The modified amino acids may be non-standard amino acids produced by post-translational modification. Examples of post-translational modification include phosphorylation, glycosylation, acylation (including, for example, acetylation, myristoylation, and palmitoylation), alkylation, carboxylation, ketonization, hydroxylation, glycosylation reactions, biotinylation, ubiquitinylation, a modification of the chemical properties (for example, beta-elimination, deimination, deamination), a structural modification (for example, formation of disulfide bridges), and modification of an amino acid resulting from the chemical reaction of binding with a cross-linking agent to form a peptide conjugate (for example, a modification of an amino group, such as change in amino group, carboxyl group or side chains)

According to an aspect of the present disclosure, there is provided a cyclic citrullinated peptide (CCP).

The term "CCP" as acronym for "cyclic citrullinated peptide" may refer to a peptide including citrulline in a cyclic structure with two cysteines linked by a disulfide bond therein.

Citrulline may be an amino acid resulting from post-translational modification of a ketimine group of arginine into a ketone group by peptidylarginine deiminase (PAD).

Peptidylarginine deiminase (PAD) as a hydrolase may hydrolyze a C—H bond of an amidine group.

For example, the peptidylarginine deiminase (PAD) may be PADI1, PADI2, PADI3, or PADI4. The peptidylarginine deiminase (PAD) may be a protein with one of SEQ ID NOS: 11 to 14.

The CCP may have an amino acid sequence with a sequence identity of about 60% or more to at least one of amino acid sequences of SEQ ID NOs: 1 and 3 to 10, for example, about 70% or more, about 80% or more, about 90% or more, about 91% or more, about 92% or more, about 93% or more, about 94% or more, about 95% or more, about 96% or more, about 97% or more, about 98% or more, about 99% or more, or about 100%. In some embodiments, the CCP may be a peptide having an amino acid sequence of one of SEQ ID NOS: 1 and 3 to 10 in which at least one, at least two, at least three, at least four, at least five, at least six, or at least seven amino acids have modified sequences.

As used herein, the term "sequence identity" of a peptide or amino acid sequence used herein refers to a degree of identity of amino acid residues of two corresponding sequences over a particular region measured after the sequences are aligned to be matched with each other as much as possible. The sequence identity is a value that is measured by comparing optimally aligned two corresponding sequences of a particular comparable region, wherein in the comparable region, a part of the sequence may be added or deleted compared to a reference sequence. In some embodiments, a percentage of the sequence identity may be calculated by comparing two optimally aligned corresponding sequences in an entire comparable region, determining the number of locations where an amino acid or a nucleic acid is identical in the two sequences to obtain the number of matched locations, dividing the number of the matched locations by the total number (that is, a range size) of all locations within a comparable range, and multiplying the result by 100 to obtain a percentage of the sequence identity. The percent of the sequence identity may be determined by using known sequence comparison programs, for example, BLASTN (NCBI), CLC MAIN WORKBENCH (CLC BIO), or MegAlign™ (DNASTAR INC.).

The peptide may be a wild type peptide identified and separated from naturally occurring sources. The peptide CCP according to any embodiments of the present disclosure may be an artificial variant including at least one amino acid having a sequence that is substituted, deleted, and/or inserted compared to at least one of the peptides including amino acid sequences of SEQ ID NOs: 1 to 10. Modification in amino acid of a wild type polypeptide or an artificial variant may include conservative amino acid substitution that does not significantly affect folding and/or activity of a protein. Examples of conservative amino acid substitution may include substitution of a basic amino acid, an acidic amino acid, a polar amino acid, a hydrophobic amino acid, an aromatic amino acid, and a smaller amino acid. The basic amino acid may be arginine, lysine, or histidine. The acidic amino acid may be glutamic acid or aspartic acid. The polar amino acid may be glutamine or asparagine. The hydrophobic amino acid may be leucine, isoleucine, valine, or methionine. The aromatic amino acid may be phenylalanine, tryptophan, or tyrosine. The smaller amino acid may be glycine, alanine, serine, or threonine. Amino acid substitutions that may lead to no change in a specific activity are known in the art.

Another type of amino acid variant in peptide may be an amino acid variant that may result from a modification in a glycosylation pattern of an amino acid. The "modification" may refer to deletion of at least one carbohydrate moiety found in the peptide and/or addition of at least glycosylation site not present in the peptide.

Typically, glycosylation of peptide may be N-linked glycosylation or O-linked glycosylation. N-linked glycosylation may refer to the attachment of carbohydrate residues to a side chain of asparagines residue. Tripeptide sequences asparagine-X-serine and asparagine-X-threonine, where X is any amino acid except proline, are the recognition sequences for enzymatic attachment of carbohydrate moiety to the asparagines side chain. Accordingly, the presence of a polypeptide with at least one of the tripeptide sequences in a polypeptide may provide a potential glycosylation site. O-linked glycosylation may refer to the attachment of one of sugar N-acetylgalactosamine, galactose, and xylose to hydroxyamino acid, serine, threonine, 5-hydroxyproline, or 5-hydroxylysine.

Addition of a glycosylation site, for example, an N-linked glycosylation site, to a peptide may be implemented by modifying the amino acid sequence of the peptide to include at least one of the above-mentioned tripeptide sequences. Addition of an 0-linked glycosylation site may be implemented by adding at least one serine or threonine residue into the sequence of an original peptide or substituting with at least one serine or threonine residue.

The CCP may be detectably labeled. The labeling may be optical labeling, electrical labeling, radioactive labeling, enzymatic labeling, or any combination thereof. The optical labeling may be implemented by using a fluorescent or phosphorescent substance. Examples of the fluorescent substance are fluorescein, rhodamine, cyanine (Cy), metalloporphyrin complex, Cy-5, and Cy-3. Examples of the fluorescein dye include 6-carboxyfluorescein (6-FAM), 2',4',1,4,-tetrachlorofluorescein (TET) 2',4',5',7',1,4-hexachlorofluorescein (HEX), 2',7' dimethoxy-4',5'-dichloro-6-carboxyrhodamine (JOE), 2'-chloro-5'-fluoro-7', 8'-fused phenyl-1,4-dichloro-6-carboxyfluorescein, and 2'-chloro-7'-phenyl-1,4-dichloro-6-carboxyfluorescein. The enzyme used in enzymatic labeling may convert a substrate into chromophoric substance).

According to another aspect of the present disclosure, there is provided a rheumatoid arthritis diagnosis composition including a CCP according to any of the embodiments as described above.

The rheumatoid arthritis diagnosis composition may further include a material required for analysis, for example, detection or quantification of a target material. For example, the material required for analysis may be an antibody or antigen-binding fragment, a cell-staining reagent, a buffer, or the like.

The rheumatoid arthritis diagnosis composition may further a substance that specifically binds to at least one different rheumatoid arthritis marker, a fragment thereof, or any substance to measure or detect the binding. The at least one different rheumatoid arthritis marker may include a rheumatoid factor (RF), an anti-CCP antibody, a C-reactive protein (CRP), a material associated with inflammation reaction, or any combination thereof.

As used herein, the term "marker" may refer to any biological index for objective measurement and evaluation of normal biological processes, disease progression, and reactivity of drugs to treatment. For example, the marker may include blood pressure, body temperature, blood glucose level, the presence of gene or generic variants, and the levels of nucleic acid, protein, peptide, bacteria, or virus.

The term "rheumatoid factor (RF)" may refer to an autoimmune antibody observed in a rheumatoid arthritis patient.

The term "C-reactive protein (CRP)" may refer to a protein used to determine the prognosis of inflammation due to its level increase during inflammation reaction.

The erythrocyte sedimentation rate (ESR) may be measured to detect a material related with inflammation reaction. The ESR refers to the rate at which red blood cells in the venous blood treated with an anticoagulating agent are separated and precipitate from plasma. The ESR may be increased with the onset of inflammation disease due to an increased level of such as fibrinogen that is able to bind to red blood cells, and thus may be used as a marker for inflammation diseases such as rheumatoid arthritis.

The rheumatoid arthritis diagnosis composition may be in any state, for example, liquid, solid, or a combination of these states.

The subject to be diagnosed may be a mammal. For example, the mammal may be a human, a mouse, a rat, a cow, a goat, a pig, a horse, a sheep, a dog, a cat, or a combination thereof.

According to another aspect of the present disclosure, there is provided a kit for diagnosing rheumatoid arthritis, the kit including a CCP according to any of the embodiments as described above. The kit may include any material that is included in a rheumatoid arthritis diagnosis composition according to any of the above-described embodiments. The kit may include a manual in which processes of using the components of the kit to diagnose rheumatoid arthritis are described. The kit may further include a reagent for diagnosing rheumatoid arthritis in a subject. For example, the reagent may include a buffer, an indicator, or a combination thereof.

According to another aspect of the present disclosure, there is provided a method of detecting an anti-cyclic citrullinated peptide (anti-CCP) antibody, the method including contacting a test sample taken from a subject and a CCP according to any of the above-described embodiments to bind an anti-CCP antibody present in the sample to the CCP, thereby forming an anti-CCP antibody-CCP complex.

The antibody may be an antibody able to bind to a peptide having an amino acid sequence with a sequence identity of about 60% or more to at least one of amino acid sequences of SEQ ID NOS: 1 and 3 to 10, for example, about 70% or more, about 80% or more, about 90% or more, about 91% or more, about 92% or more, about 93% or more, about 94% or more, about 95% or more, about 96% or more, about 97% or more, about 98% or more, about 99% or more, or about 100%.

The method may include contacting a sample taken from a subject and a CCP according to any of the above-described embodiments to bind an anti-CCP antibody present in the sample with the CCP. The contacting may be performed in a liquid medium. The liquid medium may be a sample itself in a liquid state, water, a buffer, or a combination thereof. The contacting may be performed by mixing the sample with the CCP. For example, the contacting may be performed by stirring the sample and the CCP in a container.

The subject may be the same as that described above in conjunction with the rheumatoid arthritis diagnosis composition according to an embodiment of the present disclosure.

The sample may be a biological material derived from the subject. The biological sample may be a solid tissue obtained from a fresh or stored organ, tissue, or a biopsy; blood or blood components; bodily fluids, such as amniotic fluid, peritoneal fluid, or interstitial fluid; cells; or any combinations thereof. The sample may include a compound naturally occurring without being mixed with a biological material such as preservatives, anticoagulants, buffers, fixatives, nutrients, and antibiotics. For example, the sample may be urine, mucus, saliva, tears, blood plasma, blood serum, sputum, spinal fluid, serous fluid from a pleural cavity, nipple aspirate, lymph, tracheolar fluid, intestinal juice, genitourinary tract fluid, breast milk, semen, peritoneal fluid, cystic tumor fluid, amniotic fluid, or any combinations thereof.

The CCP may be detectably labeled.

In the anti-CCP antibody detection method, the CCP and the labeling may be the same as described above in conjunction with the composition or kit for diagnosing rheumatoid arthritis.

The anti-CCP antibody detection method may include measuring a level of the anti-CCP antibody present in the sample. The measuring of the level of the anti-CCP antibody may include directly or indirectly measuring the level of the anti-CCP antibody, for example, by measuring the presence or the amount of the CCP and/or an anti-CCP antibody-CCP complex. In this case, the CCP may be labeled, so that the level of the anti-CCP antibody may be measured by detecting a signal from the labeling of the CCP.

The measuring of the level of the CCP and/or the anti-CCP antibody-CCP complex may include measuring the amount of the CCP after separation from the anti-CCP antibody-CCP complex, or measuring the amount of the CCP not separated from the anti-CCP antibody-CCP complex. The measuring may be implemented by detecting a signal from the detectable maker attached to the CCP. Separating of the CCP may be performed by centrifugation, precipitation, salting out, dialysis, filtration, chromatography, electrophoresis, or any combination thereof. Chromatography may include substitution chromatography, size-exclusion chromatography, ion-exchange chromatography, or any combination thereof. The measuring of the level of the CCP and/or the anti-CCP antibody-CCP complex may be performed by western blotting, enzyme linked immunosorbent assay (ELISA), radioimmunoassay (RIA), radioimmunodiffusion, Ouchterlony radioimmunodiffusion (ODD), rocket immunoelectrophoresis, tissue immunostaining, immunoprecipitation assay, complement fixation assay, fluorescence-activated cell sorting (FACS), protein chip, spectrometry, spectroscopy, or any combination thereof.

For example, the measuring of the level of the CCP, anti-CCP antibody, or anti-CCP antibody-CCP complex may be performed by ELISA. ELISA may include any of various types of ELISA, including a direct ELISA using a labeled antibody to detect an antigen fixed to a solid support, an indirect ELISA using a labeled (secondary) antibody to detect a capture (primary) antibody in an antigen-antibody complex in which the capture (primary) antibody is bound to an antigen fixed to a solid support, a direct sandwich ELISA using a labeled antibody to detect the antigen of an antibody-antigen complex bound to a solid support, and an indirect sandwich ELISA using a labeled secondary antibody to detect an antibody which is bound to the antigen of an antibody-antigen complex bound to a solid support.

For example, when sandwich ELISA is used, the sandwich ELISA may include the following steps: for example, coating the CCP as a primary antibody on a surface of a solid support; contacting a sample taken from a subject and the primary antibody to induce an antigen-antibody reaction; reacting a resulting product from the inducing of antigen-antibody reaction with a secondary antibody bound with an enzyme; and detecting the activity of the enzyme.

The solid support may be formed of a hydrocarbon polymer (for example, polystyrene or polypropylene), glass, metal, or gel. For example, the solid support may be a microtiter plate. The secondary antibody bound with an enzyme may include an enzyme that may catalyze a color reaction, fluorescent reaction, luminescent reaction, or infrared reaction, for example, alkaline phosphatase, β-galactosidase, horseradish peroxidase, luciferase, or cytochrome P450. For example, when the enzyme bound to the secondary antibody is alkaline phosphatase, a substrate for this enzyme bound to the secondary antibody may be a substrate for color reaction, for example, a substrate including bromochloroindolyl phosphate (BCIP), nitro blue tetrazolium (NBT), naphthol—AS-B1-phosphate, and enhanced chemifluorescence (ECF). When the enzyme bound to the secondary antibody is horseradish peroxidase, a substrate for this enzyme bound to the secondary antibody may be chloronaphthol, aminoethyl carbazole, diaminobenzidine, D-luciferin, lucigenin (bis-N-methyl acridinium nitrate), resolupin benzyl ether, luminol, an amplex red reagent (10-acetyl-3,7-dihydroxyphenoxazine), HYR (p-phenylenediamine-HCl and pyrocatechol), TMB (tetramethylbenzidine), ABTS (2,2'-azino-bis[3-ethylbenzothiazoline-6-sulphonic acid]), o-phenylenediamine (OPD), naphthol/pie Ronin, glucose oxidase, t-NBT (nitroblue tetrazolium) or m-PMS (phenzaine methosulfate).

In some embodiments, the anti-CCP antibody detection method may further include determining the subject to be at a high risk for rheumatoid arthritis if the level of the CCP, anti-CCP antibody, and/or anti-CCP antibody-CCP complex is higher than a control group sample. The control group sample may be a sample obtained from a non-rheumatoid arthritis patient or a subject with a low risk for rheumatoid arthritis.

The determining may include: comparing the amount of the anti-CCP antibody in the sample taken from the subject with the amount of the anti-CCP antibody in the control group sample; and determining the subject as a rheumatoid arthritis patient or to be at a high risk for rheumatoid arthritis if the amount of the anti-CCP antibody is higher than the amount of the anti-CCP antibody in the control group sample.

The anti-CCP antibody detection method may further include measuring the presence, amount, and/or level of at least one different rheumatoid arthritis markers, or measuring the level of a material that specifically bind to the at least one different rheumatoid arthritis markers or a fragment thereof. The different rheumatoid arthritis markers may be a RF, an anti-CCP antibody, a CRP, an ESR or a combination thereof.

The terms and elements that are referred to herein in conjunction with the anti-CCP antibody detection method according to any of the above-described embodiments and overlap with those used to describe the claimed rheumatoid arthritis diagnosis compositions or kits have the same meanings as used with regard to the claimed rheumatoid arthritis diagnosis compositions or kits.

According to another aspect of the present disclosure, there is provided a method of screening a diagnostic marker for rheumatoid arthritis, the method including: modifying an amino acid sequence in a CCP; contacting the CCP having the modified amino acid sequence with a test sample taken from a rheumatoid arthritis patient to form an anti-CCP antibody-CCP complex; and measuring the level of the anti-CCP antibody.

The modifying of the amino acid sequence may include addition, deletion, substitution, and/or post-translational modification of an amino acid.

The addition of an amino acid may be adding an amino acid in the middle of sequence, a N-terminal, a C-terminal, or both N-terminal and C-terminal of the CCP. For example, an amino acid to be added may be c-aminocaproic acid.

The substitution of an amino acid may be substituting at least one of the amino acids present at a N-terminal, a C-terminal, or between the N-terminal and C-terminal. The substitution of an amino acid may be substituting an alkaline, acidic, polar, hydrophobic, aromatic, or post-translationally modified amino acid by an amino acid having a different characteristic therefrom.

The modifying of the amino acid sequence may be modifying a sequence of at least one amino acid present between citrulline of the CCP and disulfide bond-forming cysteine in the C-terminal direction.

The screening method may further include contacting the CCP having the modified amino acid sequence with a test sample taken from a rheumatoid arthritis patient and with a control group sample.

The screening method may include determining the CCP as a candidate diagnostic marker for rheumatoid arthritis if the level of the anti-CCP antibody detected in the test sample taken from a rheumatoid arthritis patient is higher than the level of the anti-CCP antibody detected in the control group sample.

A number of ring-forming amino acids in the CCP is not limited as long as the CCP can bind to an anti-CCP antibody. For example, the number of ring-forming amino acids in the CCP may be, for example, 5, 6, 7, 8, 9, 10, 11, 12, 13, 14, 15, 16, 17, 18, 19, 20, 21, 22, 23, 24, or 25.

The screening method may further include measuring the sensitivity and/or specificity of anti-CCP antibodies for the diagnosis of rheumatoid arthritis based on the measured level of the anti-CCP antibody. The screening method may further include selecting a cut-off level of anti-CCP antibodies with an optical sensitivity and/or specificity based on a receiver operating characteristic (ROC) curve.

A ROC curve as a plot of the relation between sensitivity and specificity in a specific diagnostic test may represent the diagnostic accuracy of a specific diagnostic model. The ROC may be a graph generated by plotting sensitivity of all possible cut-off points for a specific diagnostic model on Y-axis against 1-specificity on X-axis. The specific diagnostic model may be a diagnostic model for rheumatoid arthritis in which a specific level of anti-CCP antibody is determined as a cut-off level for positivity with disease (abnormal) and/or negativity without disease (normal patients). The larger the area under the ROC curve (AUC), the higher the accuracy of the determined diagnostic model. With the assumption that a total area of the ROC curve is 1, a diagnostic model may be determined as having high accuracy when the AUC is 0.5 or greater, 0.6 or greater, 0.7 or greater, 0.8 or greater, or 0.9 or greater. A diagnostic model may be determined as a higher accuracy when it is closer to the upper left corner of the ROC.

The term "sensitivity" may refer to the probability that an individual with the disease will test positive in a specific diagnostic model.

The term "specificity" may refer to the probability that a disease-free individual will test negative in a specific diagnostic model.

The screening method may further include measuring the sensitivities and/or specificities of CCPs with modified amino acid sequences and selecting a CCP with higher sensitivity and/or specificity for the diagnosis of rheumatoid arthritis than the other CCPs with modified amino acid sequences.

The terms and elements referred to herein in conjunction with a method of screening a diagnostic marker for RA according to any of the above-described embodiments and overlap with those used to describe the claimed rheumatoid arthritis diagnosis compositions or kits, or anti-CCP antibody detection methods are understood to have the same meanings as used with regard to the claimed rheumatoid arthritis diagnosis compositions or kits, or anti-CCP antibody detection methods.

One or more embodiments of the present disclosure will now be described in detail with reference to the following examples. However, these examples are only for illustrative purposes and are not intended to limit the scope of the one or more embodiments of the present disclosure.

Example 1. Preparation of Peptides and Patient Serum Samples and Assay Methods Thereof The reagents and devices used were as follows.

Phosphate buffered saline (PBS, Cat. No: LB201-02, available from WelGene, Daejeon, Korea), Tween-20 (Cat. No: 274348) for washing, bovine serum albumin (BSA, Cat. No: A1253, available from Sigma-aldrich, St. Louis, USA), HRP-conjugated anti-human IgG antibody (Cat. No: ab6858, available from Abcam, Cambridge, UK) as a secondary antibody for anti-CCP antibody detection were purchased. A 96-well microplate (Cat. No: 439454) and a TMB substrate (Cat. No: 34021) were purchased from Thermo (Rockford, USA). Peptides were synthesized by Peptron (Daejon, Korea). The results from enzyme linked immunosorbent assay (ELISA) were analyzed using a microplate reader (available from Bio-rad, Hercules, USA).

Table 1 shows sequence information of the used peptides, including usual and unusual amino acids such as citrulline and aminocaproic acid.

TABLE 1

| SEQ ID No. | Peptide | Sequence information |
|---|---|---|
| 1 | CCP | HCHQESTXGRSRGCG |
| 2 | RF | EGLHNHY |
| 3 | HSH15 | HSHQESTXGRSRGSG |
| 4 | ZZH17 | ZZHSHQESTXGRSRGSG |
| 5 | HSH17 | HSHQESTXGRSRGSGZZ |
| 6 | ZZH19 | ZZHSHQESTXGRSRGSGZZ |
| 7 | CCP10P | HCHQESTXGPSRGCG |
| 8 | CCP11A | HCHQESTXGRARGCG |
| 9 | CCP12P | HCHQESTXGRSPGCG |
| 10 | CCPPAP | HCHQESTXGPAPGCG |

* X indicates citrulline, and Z indicates aminocaproic acid.
* Peptides with SEQ ID NOS. 1, and 7 to 10 may be in cyclic form due to cysteines 2 and 14 forming disulfide bond.

Sandwich enzyme linked immunosorbent assay (ELISA) using the peptides of Table 1 were performed on the samples from 4 test groups. Serum samples of RA patients (30 subjects), OA patients (15 subjects), SLE patients (25 subjects), and control group samples (25 normal subjects) were prepared.

TABLE 2

| Type of disease | No. of patients | Age | Gender (Female/Male) |
|---|---|---|---|
| Rheumatoid arthritis (RA) | 30 | 51.21 (25-74) | 22/8 |
| Osteoarthritis (OA) | 15 | 47.27 (20-75) | 13/2 |
| Systemic lupus erythemathode (SLE) | 25 | 38.32 (22-83) | 24/1 |
| Normal control group | 25 | 52.56 (29-76) | 15/10 |

Each of the prepared peptides of Table 1 was diluted with PBS to about 10 µg/ml, added by about 100 µl to a microplate, and then coated at about 4° C. overnight, followed by adding about 200 µl of BSA solution (10 mg/mL) to each well of the peptide coated microplate to block at room temperature for about 1 hour, and washing the microplate with a PBS including about 0.1% of Tween-20 three times to use the microplate it in this assay. The patient samples and normal control group sample were diluted by 200 times and added triplet by about 100 µl to the wells of the peptide-coated microplate. After being cultured at room temperature for about 1 hour, the resulting microplate was washed three times in the same manner as the above-described washing. To detect autoimmune antibodies in the samples, 100 µl of an anti-human IgG antibody solution (500 nm/mL) was added to each cell of the microplate and incubated at room temperature for about 1 hour, followed by washing three times in the same manner as the above-described washing. After 100 µl of a TMB substrate solution was added thereto and reacted at room temperature for about 30 minutes, finally 100 µl of a 2M sulfuric acid solution was added as a stop solution to terminate the reaction, followed by absorbance measurement at a wavelength of about 450 nm using a microplate reader.

Example 2. Identification of Binding Site of CCP to Antibody by Using Modified Peptide Obtained by Adding Aminocaproic Acid to Terminal of CCP Autoimmune antibody levels in the blood samples of normal patients and various types of arthritis patients were analyzed by enzyme linked immunosorbent assay (ELISA) using the peptides of SEQ ID NOS. 1 to 6 shown in Table 1.

Aminocaproic acid may specifically bind to a polystyrene resin substrate. This characteristics of aminocaproic acid may be utilized to identify major binding sites in the peptide sequence of CCP for autoimmune antibodies present in the bloods of a RA patient. For example, a modified CCP may be prepared by substituting disulfide bond-forming cysteine in CCP with serine to obtain a linearlized CCP without disulfide bond and adding aminocaproic acid to one or both of N- and C-terminals of the linearlized CCP to have a structure with N- or/and C-terminals able to bind to the microplate. If a modified CCP with immobilized N-terminal and free C-terminal presents higher binding affinity than that of a modified CCP with immobilized C-terminal and free N-terminal, the C-terminal of CCP may be identified as a binding site with high binding strength to autoimmune antibody of CCP.

(1) Identification of Role of CCP's Cyclic Structure in Binding to CCP's Autoimmune Antibody FIGS. 1A, 1B, 1C, 1D, 1E, and 1F are graphs illustrating the levels of autoimmune antibody in the blood samples of the normal patients and various types of arthritis patients, wherein X-axis denotes samples and Y-axis denotes absorbance. The results of FIGS. 1A, 1B, 1C, 1D, 1E, and 1F are the results of assay using CCP, RF, HSH15, ZZH17, HSH17, and ZZH19, respectively, wherein HSH15 is a modified peptide obtained by substituting disulfide bond-forming cysteine in CCP with serine to eliminate disulfide bond, ZZH17 is a modified peptide obtained by adding aminocaproic acid to N-terminal of HSH15, HSH17 is a modified peptide obtained by adding aminocaproic acid to C-terminal of HSH15, and ZZH19 is a modified peptide obtained by adding aminocaproic acid to N- and C-terminals of HSH15.

The average absorbance in each sample calculated based on the results of FIGS. 1A to 1F, and statistical significances (p-value, %) with respect to normal patients calculated using t-test are shown in Table 3.

TABLE 3

| Peptide | RA | | OA | | SLE | | Normal |
|---|---|---|---|---|---|---|---|
| | Average (absorbance) | P value | Average (absorbance) | P value | Average (absorbance) | P value | Average (absorbance) |
| CCP | 0.2522 | <0.0001 | 0.2314 | <0.0001 | 0.2347 | <0.0001 | 0.0874 |
| RF | 0.2534 | 0.0002 | 0.2791 | 0.0003 | 0.3417 | <0.0001 | 0.1484 |
| HSH15 | 0.1942 | <0.0001 | 0.2277 | 0.0001 | 0.2704 | <0.0001 | 0.1067 |
| ZZH17 | 0.2667 | <0.0001 | 0.2344 | <0.0001 | 0.2738 | <0.0001 | 0.1102 |
| HSH17 | 0.2681 | <0.0001 | 0.2916 | <0.0001 | 0.3569 | <0.0001 | 0.1412 |
| ZZH19 | 0.4008 | <0.0001 | 0.3069 | <0.0001 | 0.3693 | <0.0001 | 0.1609 |

The absorbance values of all the arthritis patient samples analyzed using the various peptides were statistically significantly higher than those of the normal control group samples. ZZH19 is a modified peptide that exposes citrulline moiety like CCP when coated on a microplate. the RA patient sample treated with ZZH19 was found to represent an average absorbance of about 0.4008, which was higher than an average absorbance of about 0.3069 in the OA patient sample and an average absorbance of about 0.3693 in the SLE patient sample. ZZH19 of the other modified CCPs including aminocaproic acid was also found to have a highest average absorbance in the RA patient samples, indicating that a cyclic structure with exposed citrulline may play a significant role in the diagnosis of RA.

(2) Identification of Role of C-Terminal of CCP in Binding to CCP's Autoimmune Antibody Referring to Table 3, HSH17 with exposed N-terminal represents an average absorbance of about 0.2681 in the RA patients, which was lower than an average absorbance of about 0.2916 in the OA patients, and about 0.3569 in the SLE patients. Meanwhile, ZZH17 with exposed C-terminal was found to represent an average absorbance of about 0.2667 in the RA patient samples, which was higher than an average absorbance of about 0.2344 in the OA patient samples.

Figure 2A:
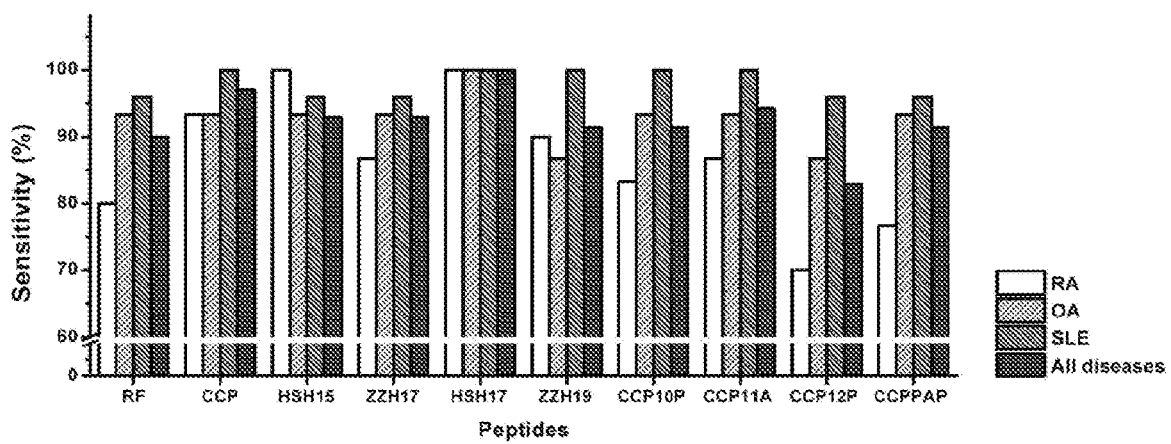
FIGS. 2A and 2B are graphs of sensitivity and specificity, respectively, of RF, CCP, and modified CCPs with respect to arthritis.
Figure 2B:
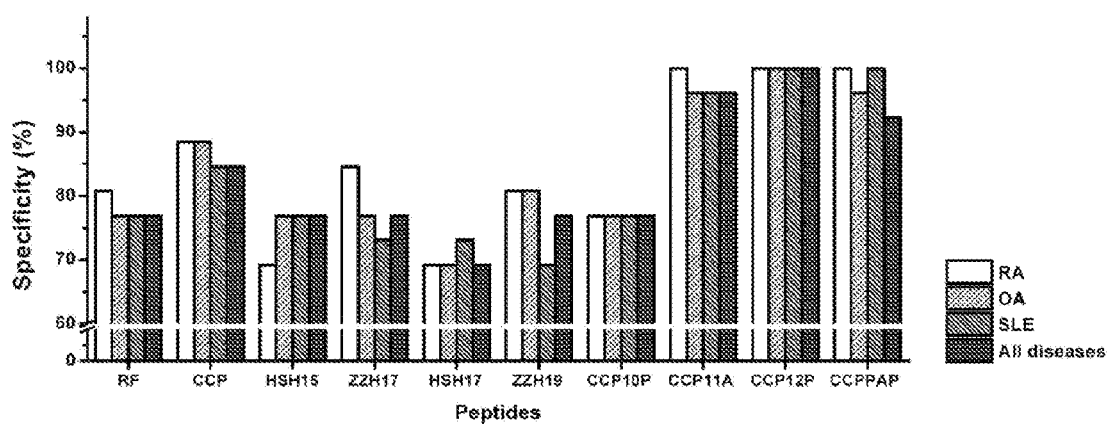
Figure 3A:
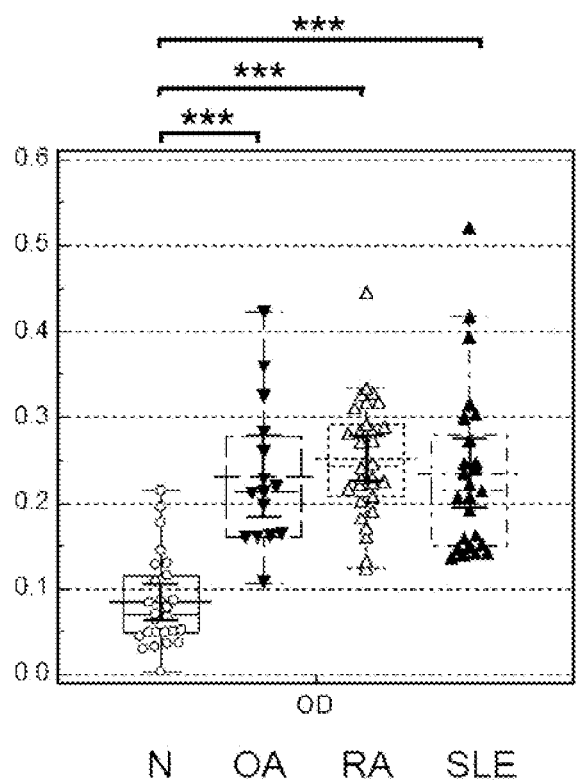
FIGS. 3A to 3E are graphs illustrating the blood autoimmune antibody levels in arthritis patients and normal patients detected using C-terminal sequence-modified CCPs, as a result of enzyme linked immunosorbent assay (ELISA)
Figure 3B:
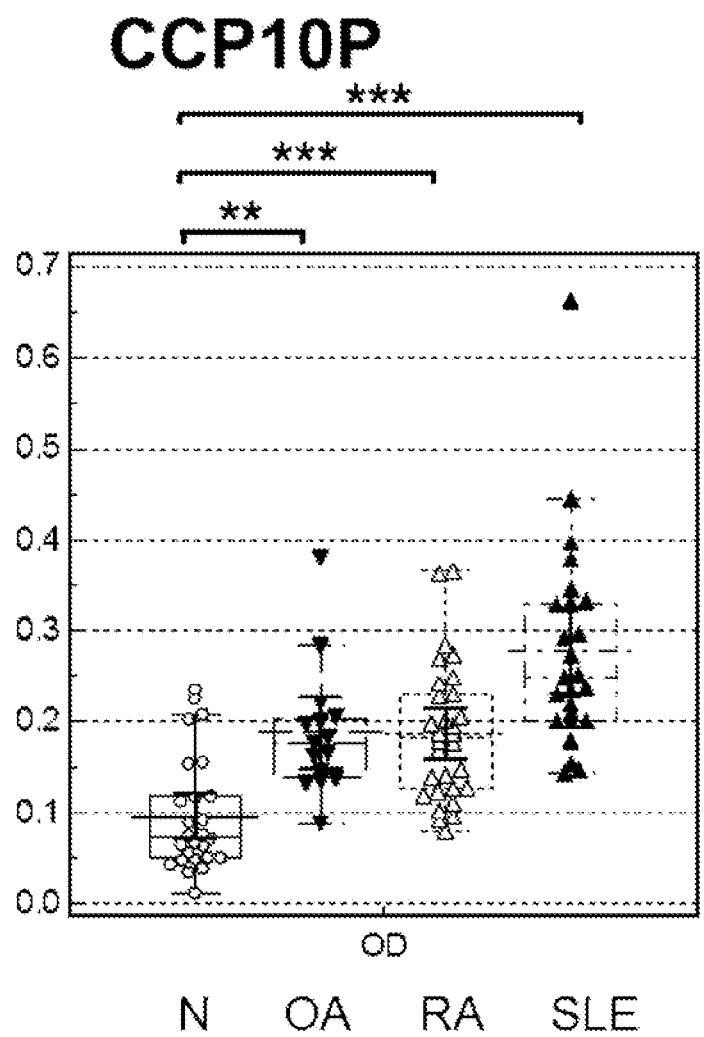
Figure 3C:
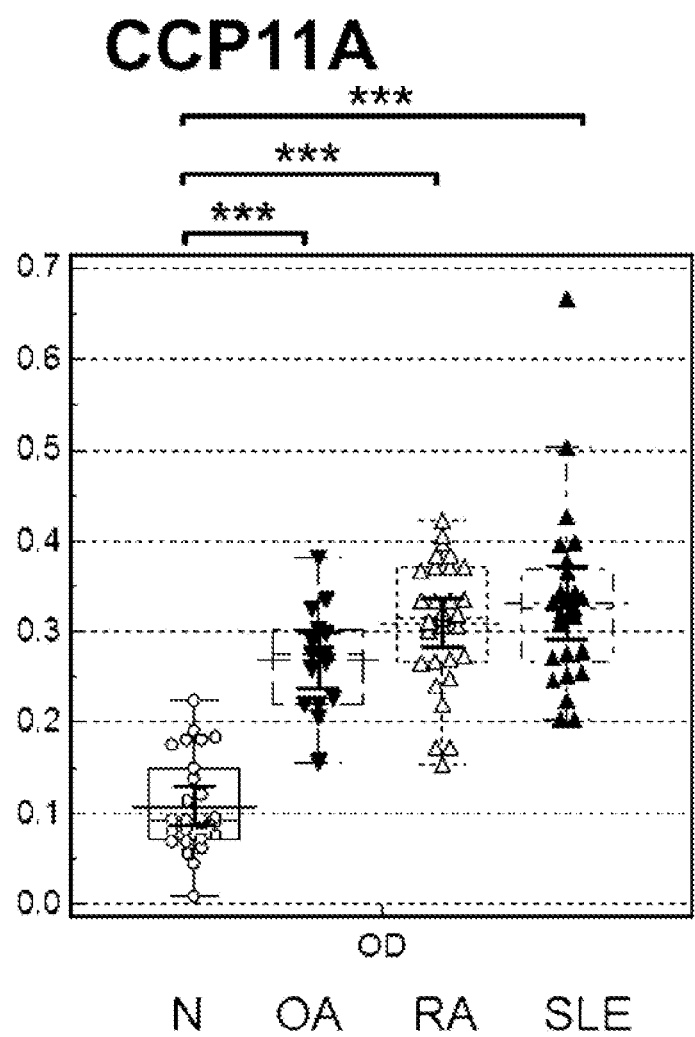
Figure 3D:
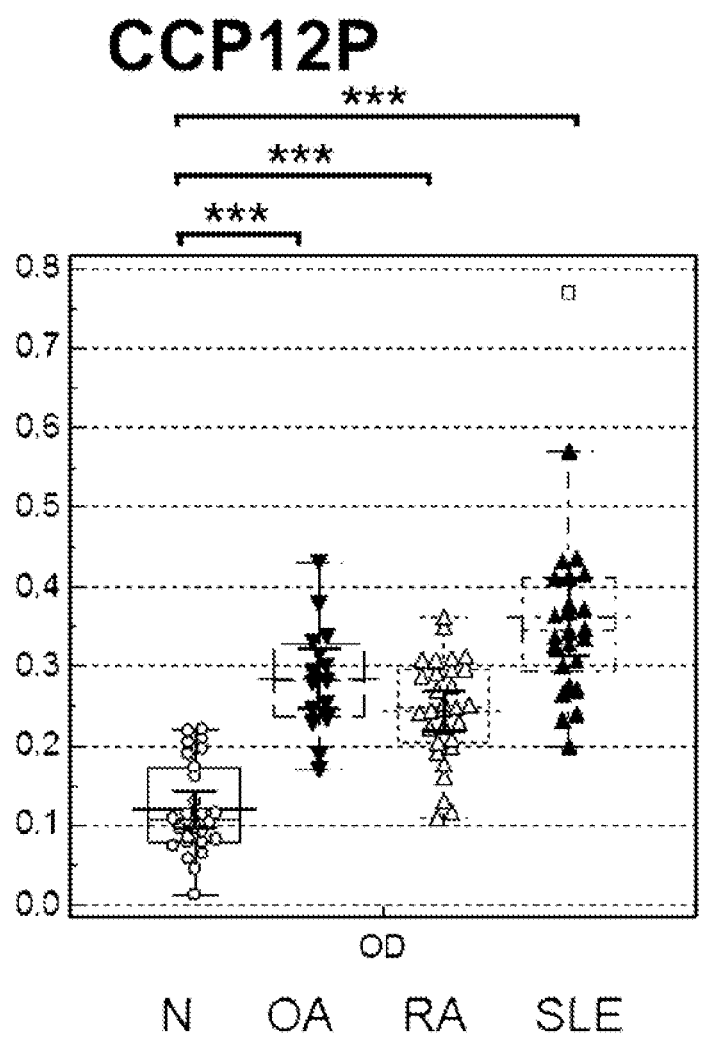
Figure 3E:
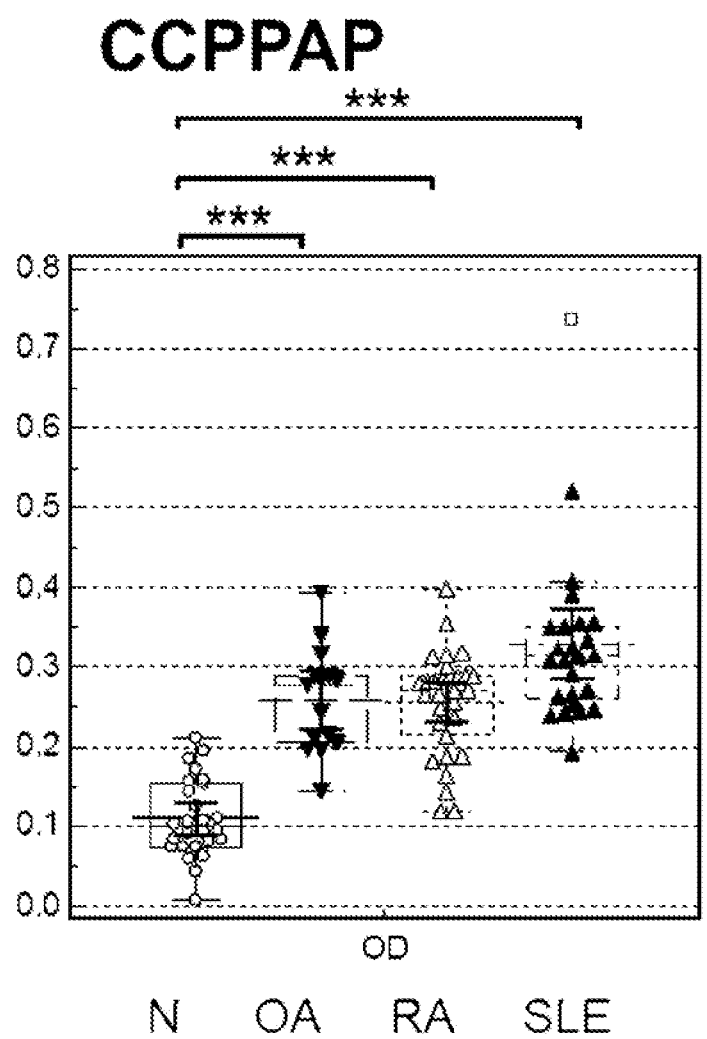

FIGS. 2A and 2B are graphs of sensitivity and specificity, respectively, of the peptides treated in the samples of various types of arthritis patients, calculated based on the ROC curves plotted using the results of Table 3. According to an autoimmune antibody detection assay using the CCP, the results of FIGS. 3A to 3E and statistical significances (p-value, %) with respect to normal patients calculated using t-test are shown in Table 4.

TABLE 4

| Peptide | RA | | OA | | SLE | | Normal |
| --- | --- | --- | --- | --- | --- | --- | --- |
| | Average (absorbance) | P value | Average (absorbance) | P value | Average (absorbance) | P value | Average (absorbance) |
| CCP | 0.2522 | <0.0001 | 0.2314 | <0.0001 | 0.2347 | <0.0001 | 0.0874 |
| CCP10P | 0.1870 | <0.0001 | 0.1875 | 0.0002 | 0.2777 | <0.0001 | 0.0994 |
| CCP11A | 0.3091 | <0.0001 | 0.2689 | <0.0001 | 0.3321 | <0.0001 | 0.1125 |
| CCP12P | 0.2445 | <0.0001 | 0.2847 | <0.0001 | 0.3619 | <0.0001 | 0.1250 |
| CCPPAP | 0.2549 | <0.0001 | 0.2591 | <0.0001 | 0.3287 | <0.0001 | 0.1140 |

CCP was found to have a sensitivity of about 93.3%, about 93.3%, and about 100% in the RA, OA, and SLE patient samples, respectively, and was found to have a specificity of about 88.5, about 88.5, and about 84.6 in the RA, OA, and SLE patient samples, respectively. RF was found to have a lower sensitivity and lower specificity than CCP. HSH17 was found to have a highest sensitivity of about 100% in all of the RA, OA, and SLE patient samples, while the aminocaproic acid-added modified peptides, including HSH17, were found to have a lower specificity than CCP in the RA patient samples. HSH17, although was highest insensitivity, was found to have a relatively low specificity of about 69.2%, 73.1%, and 69.2% in the RA, OA, and SLE patient samples, respectively. ZZH19 immobilized on a microplate in a similar pattern as CCP and ZZH17 with N-terminal immobilized on a microplate were found to have a relatively high specificity of about 84.6% and about 80.8%, respectively, when treated in the RA patient samples. Therefore, it was identified that the C-terminal domain of amino acid sequence of CCP may play an important role in the binding of autoimmune antibodies.

Example 3. Identification of Autoimmune Antibody Level in Arthritis Patients Detected Using C-Terminal Sequence-Modified CCP and Statistical Significance Test Thereon Autoimmune antibody levels in the blood samples of normal patients and various arthritis patients were analyzed by ELISA using the peptides of SEQ ID NOS. 7 to 10 shown in Table 1.

In particular, novel candidate diagnostic markers for rheumatoid arthritis were prepared by modifying a hydrophilic amino acid sequence in the C-terminal domain of CCP identified in Example 2 into a hydrophobic amino acid. The 10th amino acid arginine and 12th amino acid proline of CCP in the C-terminal direction from the 8th amino acid citrulline of CCP were substituted by proline to construct "CCP10P" and "CCP12P", respectively. The 11th amino acid serine was substituted by alanine to construct "CCP11A", and the $10^{th}$, $11^{th}$, and $12^{th}$ amino acids were substituted by proline, alanine, and proline, respectively, to construct "CCPPAP". The autoimmune antibody detection ability of these constructed peptides in various types of arthritis patients were analyzed.

FIGS. 3A, 3B, 3C, 3D, and 3E are graphs illustrating the levels of autoimmune antibody in the blood samples of the normal patients and various types of arthritis patients, detected using the peptides of SEQ ID NOS. 7 to 10 of Table 1. The average absorbance in each sample calculated based on the results of FIGS. 3A to 3E and statistical significances (p-value, %) with respect to normal patients calculated using t-test are shown in Table 4.

The absorbance values of all the arthritis patient samples analyzed using the various peptides were statistically significantly higher than those of the normal control group samples. CCP10P was found to represent an average absorbance of about 0.1870 in the RA patients, which was lower than an average absorbance of about 0.1875 in the OA patients and an average absorbance of about 0.2777 in the SLE patients. CCP12P and CCPPAP were both found to represent a lower average absorbance in the RA patients than in the OA and SLE patients. However, CCP11A was found to have an average absorbance of about 0.3094 in the RA patients, which was higher than an average absorbance of about 0.2689 in the OA patients.

CCP11A, CCP12P, and CCPPAP were found to have a high specificity of about 100% with respect to the RA, and in particular, CCP11A with substituted 11th amino acid had about 11.5% higher specificity than CCP. However, CCP10P with substituted 10th amino acid was found to have a specificity of about 76.9%, which was about 11.6% lower than CCP, indicating that the 10th amino acid arginine of CCP is an important sequence in the diagnosis of rheumatoid arthritis.

Figure 4A:
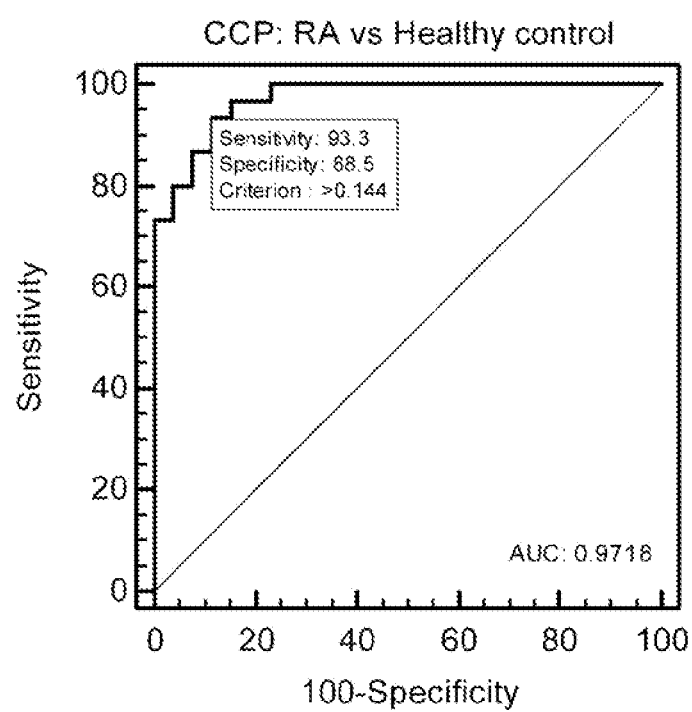
FIGS. 4A, 4B, and 4C are receiver operating characteristic (ROC) curves of CCP, and two modified CCPs, respectively, in RA patient samples with respect to normal patient samples.
Figure 4B:
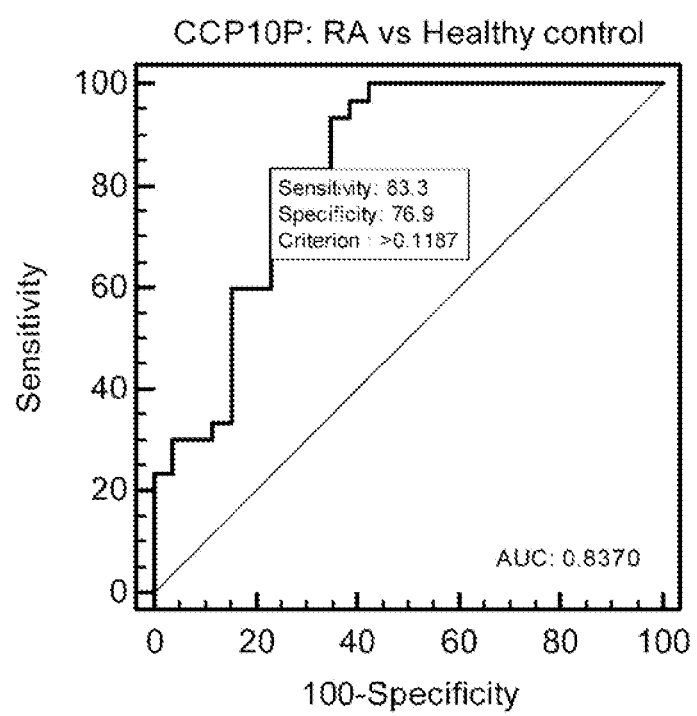
Figure 4C:
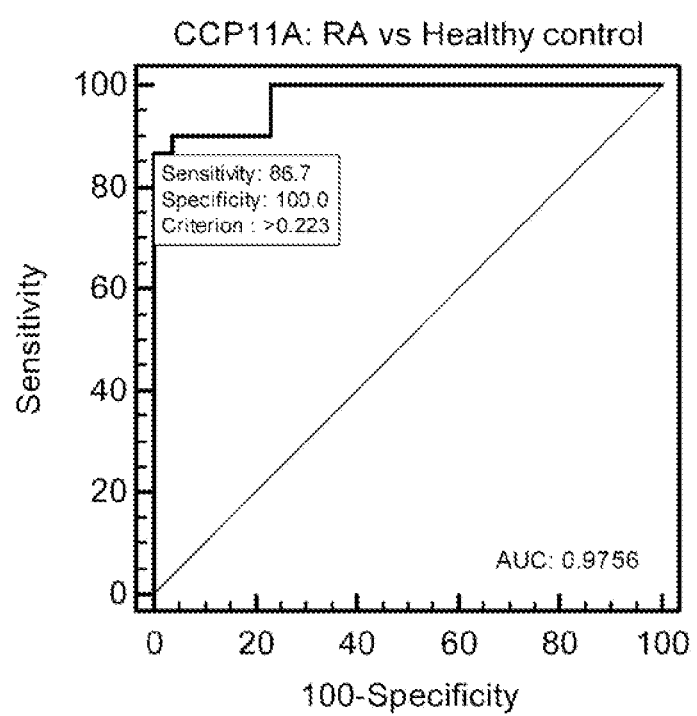
Figure 4D:
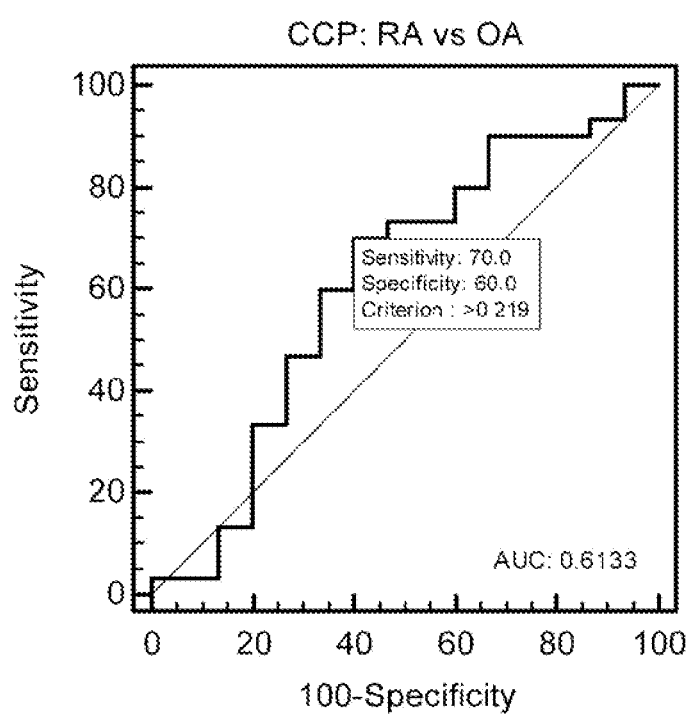
FIGS. 4D, 4E, and 4F are ROC curves of CCP and two modified CCPs, respectively, in RA patient samples with respect to osteoarthritis (OA) patient samples.
Figure 4E:
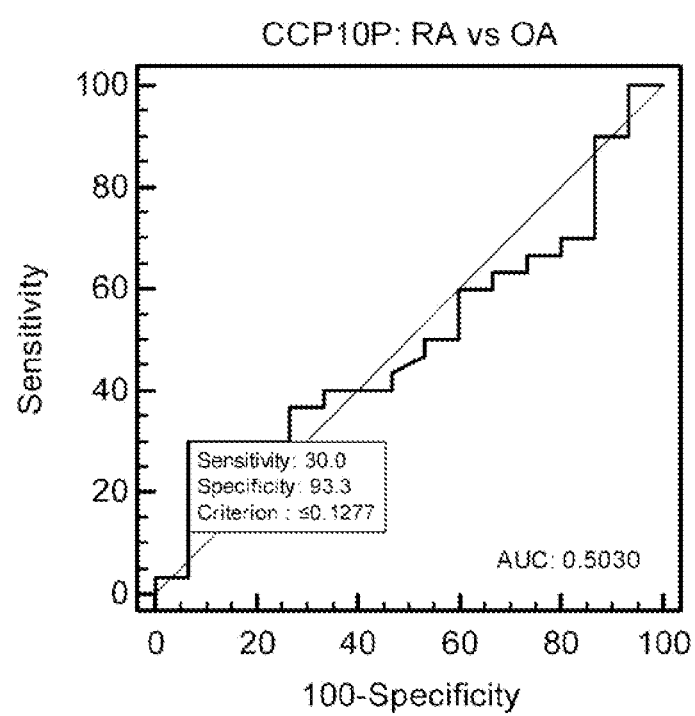
Figure 4F:
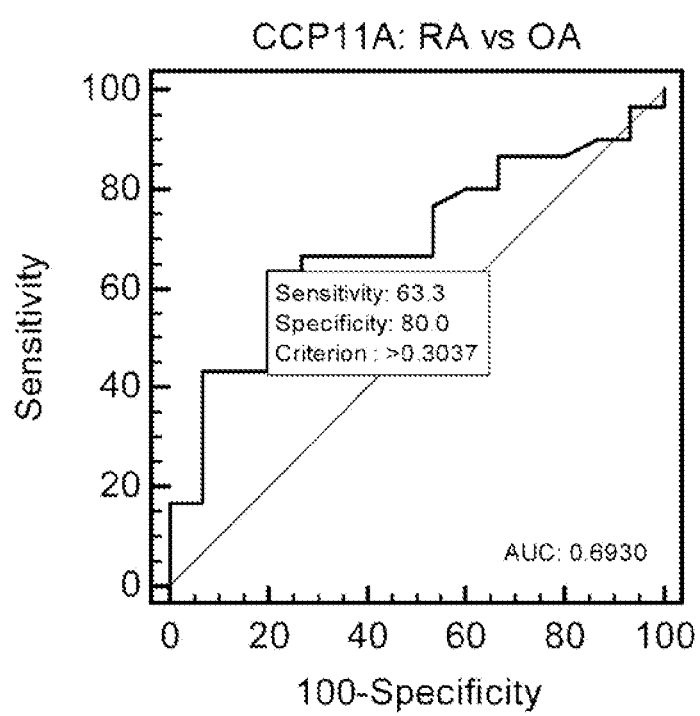

FIGS. 4A, 4B, and 4C show ROC curves of CCP, and CCP10P and CCP11A as modified CCPs including substituted amino acid, respectively, in RA patient samples with respect to normal patient samples. FIGS. 4D, 4E, and 4F show ROC curves of CCP, and CCP10P and CCP11A, respectively, in RA patient samples with respect to OA patient samples. AUCs, positive prediction rates (PPR, %), and negative prediction rates (NPR, %) obtained from the ROC curves of FIGS. 4A to 4F are shown in Table 5.

TABLE 5

| Peptide | Control group | Sensitivity (%) | Specificity (%) | AUC | PPR (%) | NPR (%) |
| --- | --- | --- | --- | --- | --- | --- |
| CCP | Normal | 93.3 | 88.5 | 0.9718 | 93.3 | 88 |
| | OA | 70.0 | 60.0 | 0.6133 | 70 | 60 |
| CCP10P | Normal | 83.3 | 76.9 | 0.8370 | 83.3 | 76 |
| | OA | 30.0 | 93.3 | 0.5030 | 30 | 93.3 |
| CCP11A | Normal | 86.7 | 100.0 | 0.9756 | 86.7 | 100 |
| | OA | 63.3 | 80.0 | 0.6930 | 63.3 | 80 |

Referring to Table 5, CCP11A had an AUC of about 0.9756 in RA patients with respect to normal patient samples, which was larger than that of CCP by about 0.0038, and an AUC of about 0.6930 with respect to OA patient samples, which was larger than a CCP's AUC of about 0.6133 by about 0.0797. Specificity and NPR, which are known as the core factors that determine the accuracy or reliability of a diagnostic assay, CCP11A were higher than those of CCP in the detection of RA with respect to both normal and OA.

Figure 5A:
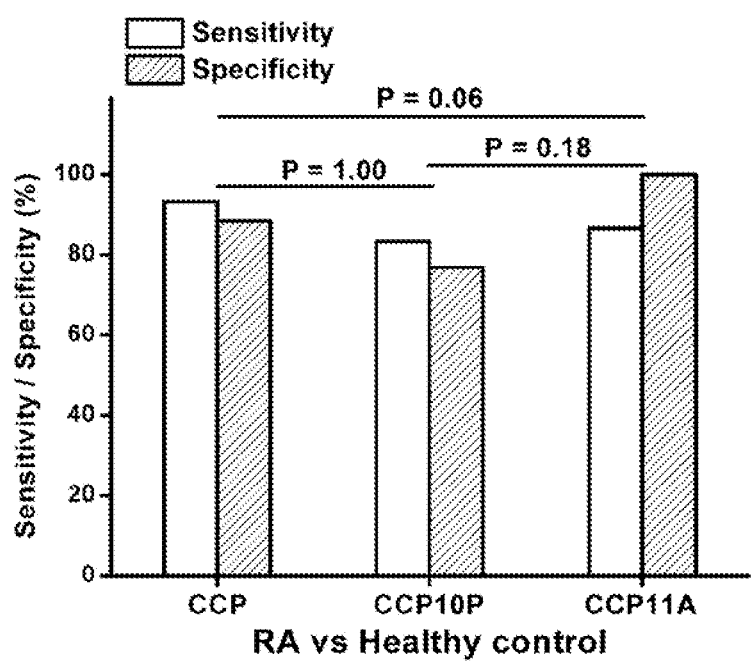
FIGS. 5A and 5B are graphs illustrating sensitivity and specificity of the tests using CCP and two modified CCPs, and statistical significances thereof in the diagnosis for RA with respect to normal (FIG. 5A) and OA patient samples (FIG. 5B) as controls.
Figure 5B:
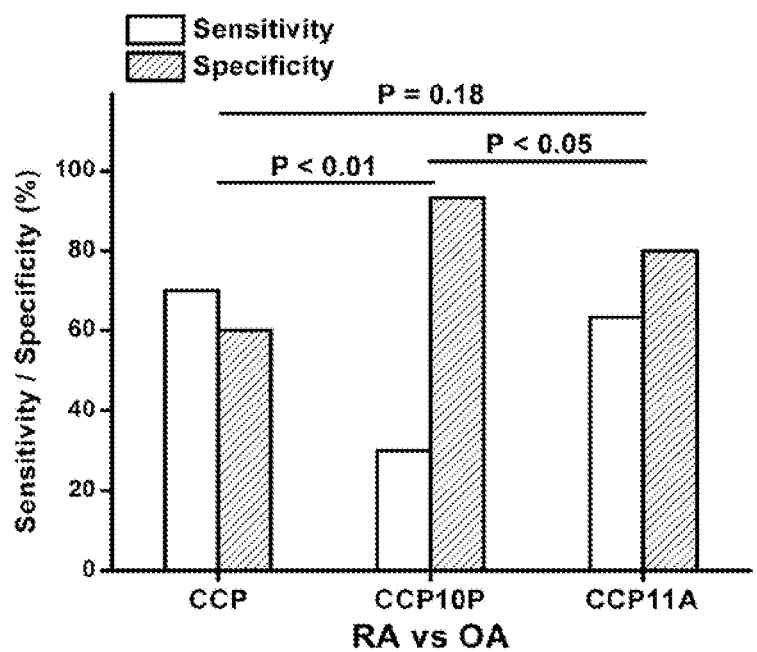

FIGS. 5A and 5B are graphs illustrating sensitivity and specificity of CCP, CCP10P, and CCP11A, and statistical significances thereof in the diagnosis for RA with respect to normal (FIG. 5A) and OA patient samples (FIG. 5B) as controls.

The statistical significances were calculated using the McNemer test. The McNemer test is a test on a 2×2 table to calculate a difference between paired two tests and a statistical significance level. Referring to FIG. 5A, a p-value between the results of the two assays with CCP and CCP10P in the RA patient samples with respect to normal patient samples as control group was 1, and a difference therebetween was 0.0%, indicating that the results of the two assays with CCP and CCP10P are statistically very similar. Referring to FIG. 5B, a p-value between the results of the two assays with CCP and CCP10P in the RA patient samples with respect to OA patient samples as control group was about 0.004, and a difference therebetween was about 37.78%. A p-value between the results of the two assays with CCP and CCP11A in the RA patient samples with respect to OA patient samples was about 0.04, and a difference therebetween was about 26.67%. Therefore, the results of the assay with CCP10P had a statistically significantly difference from the assay results with CCP and CCP11A.

As described above, according to the one or more of the above embodiments of the present invention, a CCP may be used to efficiently diagnose rheumatoid arthritis. A rheumatoid arthritis diagnosis composition or kit (including the CCPs) may be used to efficiently diagnose rheumatoid arthritis. A method of detecting an anti-CCP antibody in a subject may efficiently provide information required in the diagnosis for rheumatoid arthritis. An efficient method of screening novel diagnostic markers for rheumatoid arthritis is provided.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A peptide consisting of the amino acid sequence of SEQ ID NO: 8, wherein the peptide has a cyclic structure with two cysteines linked by a disulfide bond, and is detectably labelled.

2. A rheumatoid arthritis diagnosis composition comprising the peptide of claim 1.

3. A method of detecting an anti-cyclic citrullinated peptide (anti-CCP) antibody, the method comprising:
   forming an anti-CCP antibody-peptide complex by contacting a sample taken from a subject with the peptide of claim 1 to bind an anti-cyclic citrullinated peptide (CCP) antibody present in the sample to the peptide; and detecting a level of the anti-CCP antibody-peptide complex in the sample.

4. The method of claim 3, further comprising determining that the subject is at high risk for rheumatoid arthritis if the level of the anti-CCP antibody-peptide complex in the sample is higher than a level of anti-CCP antibody-peptide complex in a control group sample.

5. The method of claim 3, further comprising measuring a level of at least one different rheumatoid arthritis marker in the sample.

6. The method of claim 5, wherein the measuring of the level of at least one different rheumatoid arthritis marker comprises measuring a level of a rheumatoid factor (RF), an anti-CCP antibody, or a C-reactive protein (CRP) or measuring the erythrocyte sedimentation rate (ESR).

7. The method of claim 3, wherein the detecting of the level of the anti-CCP antibody-peptide complex is performed using western blotting, enzyme linked immunosorbent assay (ELISA), radioimmunoassay (RIA), radioimmunodiffusion, Ouchterlony radioimmunodiffusion (ODD), rocket immunoelectrophoresis, tissue immunostaining, immunoprecipitation assay, complement fixation assay fluorescence-activated cell sorting (FACS), protein chip, or a combination thereof.

* * * * *